(12) United States Patent
Allegretti et al.

(10) Patent No.: US 7,939,521 B2
(45) Date of Patent: May 10, 2011

(54) 2-ARYLPROPIONIC ACID DERIVATIVES AND PHARMACEUTICAL COMPOSITIONS CONTAINING THEM

(75) Inventors: Marcello Allegretti, L'Aquila (IT); Riccardo Bertini, L'Aquila (IT); Andrea Beccari, L'Aquila (IT); Alessio Moriconi, L'Aquila (IT); Andrea Aramini, L'Aquila (IT); Cinzia Bizzarri, L'Aquila (IT); Francesco Colotta, L'Aquila (IT)

(73) Assignee: DompePHA.R.MA S.p.A., L'Aquila (IT)

( * ) Notice: Subject to any disclaimer, the term of this patent is extended or adjusted under 35 U.S.C. 154(b) by 811 days.

(21) Appl. No.: 11/721,971

(22) PCT Filed: Dec. 13, 2005

(86) PCT No.: PCT/EP2005/056742
§ 371 (c)(1),
(2), (4) Date: Jun. 15, 2007

(87) PCT Pub. No.: WO2006/063999
PCT Pub. Date: Jun. 22, 2006

(65) Prior Publication Data
US 2008/0312293 A1 Dec. 18, 2008

(30) Foreign Application Priority Data
Dec. 15, 2004 (EP) .................... 04029684

(51) Int. Cl.
*A61K 31/55* (2006.01)
*C07D 487/00* (2006.01)

(52) U.S. Cl. .................. 514/212.07; 540/523

(58) Field of Classification Search ................. 544/322; 540/523; 514/212.07
See application file for complete search history.

(56) References Cited

FOREIGN PATENT DOCUMENTS

| WO | WO-00/24710 A | 5/2000 |
|---|---|---|
| WO | WO-01/58852 A | 8/2001 |
| WO | WO-02/068377 A | 9/2002 |

OTHER PUBLICATIONS

Chinese Office Action issued Mar. 16, 2010, Appl. No. 200580048026.2.
New Zealand Office Action issued Jun. 19, 2009, Appl. No. 555502.
Russian Office Action issued Dec. 1, 2009, Appl. No. 2007126825/04(029201).
Pellas, T. C., "C5a Receptor Antagonists," Current Pharma. Design, vol. 5, pp. 737-755 (1999).

*Primary Examiner* — Taofiq A Solola
(74) *Attorney, Agent, or Firm* — Birch, Stewart, Kolasch & Birch, LLP

(57) ABSTRACT

The present invention relates to selected (R)-2-phenyl-propionamides and (R)-2-phenyl-sulfonamides with a hydrogen bond acceptor atom/group in a well defined position in the chemical space. These compounds show a surprising potent inhibitory effect on C5a induced human PMN chemotaxis. The compounds of the invention absolutely lack of CXCL8 inhibitory activity. Said compounds are useful in the treatment of pathologies depending on the chemotactic activation of neutrophils and monocytes induced by the fraction C5a of the complement. In particular, the compounds of the invention are useful in the treatment of sepsis, psoriasis, rheumatoid arthritis, ulcerative colitis, acute respiratory distress syndrome, idiopathic fibrosis, glomerulonephritis and in the prevention and treatment of injury caused by ischemia and reperfusion.

7 Claims, 3 Drawing Sheets

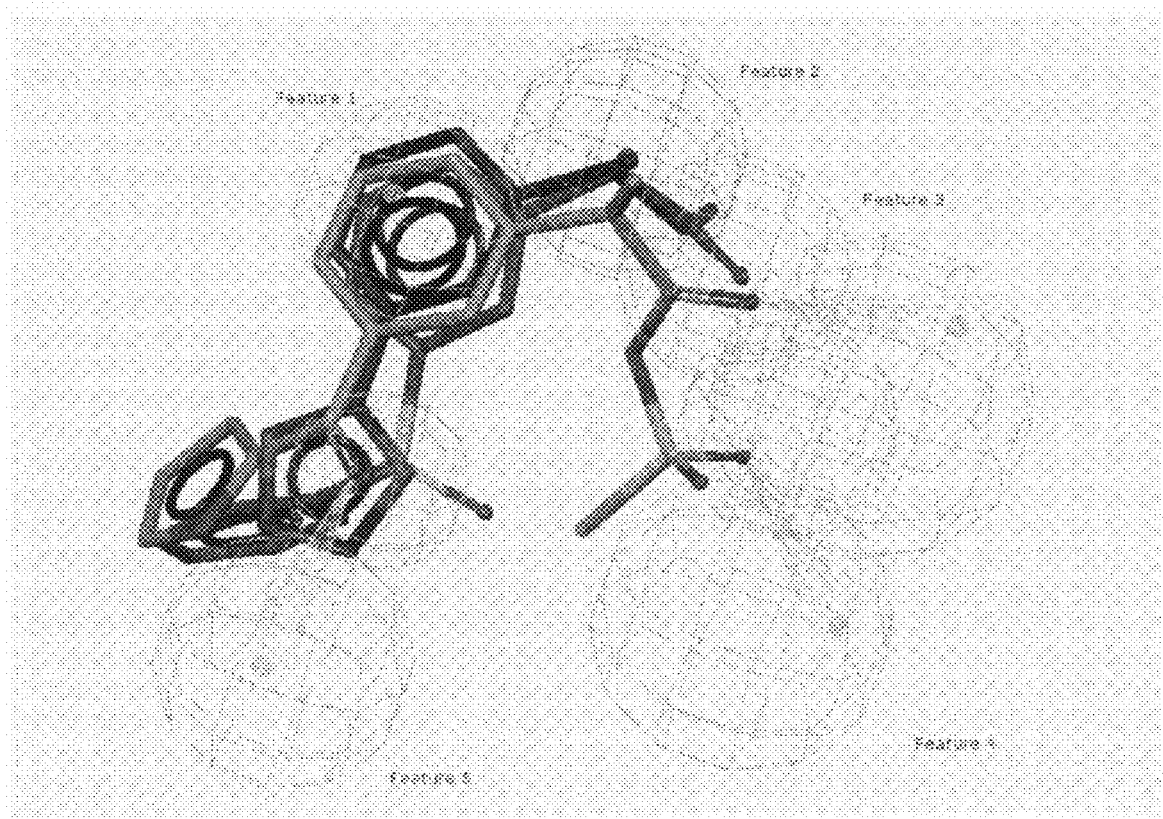

2-ARYLPROPIONIC ACID DERIVATIVES AND PHARMACEUTICAL COMPOSITIONS CONTAINING THEM

This application is the national stage of International Application PCT/EP2005/056742, filed Dec. 13, 2005, which claims priority under 35 USC §119(a)-(d) of European Application No. EP 04029684.0 filed on Dec. 15, 2004.

BRIEF DESCRIPTION OF THE INVENTION

The present invention relates to novel compounds useful in the inhibition of the chemotactic activation induced by the fraction C5a of complement. Said compounds are useful in the treatment of pathologies depending on the chemotactic activation of neutrophils and monocytes induced by the fraction C5a of the complement. In particular, the compounds of the invention are useful in the treatment of sepsis, psoriasis, rheumatoid arthritis, ulcerative colitis, acute respiratory distress syndrome, idiopathic fibrosis, glomerulonephritis and in the prevention and treatment of injury caused by ischemia and reperfusion.

STATE OF THE ART

In response to immunologic and infective events, activation of the complement system mediates amplification of inflammatory response both via direct membrane action and via release of a series of peptide fragments, generally known as anaphylatoxins, generated by enzymatic cleavage of the C3, C4 and C5 complement fractions. These peptides include C3a and C4a, both of 77 aminoacids; in turn, C5 convertase cleaves the C5 complement fraction to give the glycoprotein C5a of 74 aminoacids.

The C5a peptide fragment of the complement has been defined as the "complete" pro-inflammatory mediator due to its chemotactic and inflammatory activity. In fact, other inflammatory mediators such as selected cytokines (IL-8, MCP-1 and RANTES, for example) are highly selective towards self-attracted cells, while others such as histamine and bradykinin are only weak chemotactic agents.

Convincing evidences support the involvement of C5a, in vivo, in several pathological conditions including ischemia/reperfusion, autoimmune dermatitis, membrane-proliferative idiopathic glomerulonephritis, airway irresponsiveness and chronic inflammatory diseases, ARDS and CODP, Alzheimer's disease, juvenile rheumatoid arthritis (N. P. Gerard, Ann. Rev. Immunol., 12, 755, 1994).

In view of the neuro-inflammatory potential of C5a/C5a-desArg generated by both local complement production and amyloid activation joined with astrocyte and microglia chemotaxis and activation directly induced by C5a, complement inhibitors have been proposed for the treatment of neurological diseases such as Alzheimer's disease (McGeer & McGeer P. L., Drugs, 55, 738, 1998).

Furthermore, the control of the synthesis of complement fractions is considered a promising therapeutic target in the treatment of shock and in the prevention of rejection during organ transplant (multiple organ failure and hyperacute graft rejection) (Issekutz A. C. et al., Int. J. Immunopharmacol, 12, 1, 1990; Inagi R. et at., Immunol. Lett., 27, 49, 1991). More recently, inhibition of complement fractions has been reported to be involved in the prevention of native and transplanted kidney injuries taking account of complement involvement in the pathogenesis of both chronic interstitial and acute glomerular renal injuries. (Sheerin N. S. & Sacks S. H., Curr. Opinion Nephrol. Hypert., 7, 395, 1998).

Characteristic neutrophil accumulation occurs in acute and chronic pathologic conditions, for example in the highly inflamed and therapeutically recalcitrant areas of psoriatic lesions. Neutrophils are chemotactically attracted and activated by the synergistic action of chemokines, IL-8 and Gro-α released by the stimulated keratinocytes, and of the C5a/C5a-desArg fraction produced through the alternative complement pathway activation (T. Terui et al., Exp. Dermatol., 9, 1, 2000). We have recently described a novel class of "omega-aminoalkylamides of R-2-aryl-propionic acids" as inhibitors of the chemotaxis of polymorphonucleate and mononucleate cells" (WO 02/068377). The novel class includes compounds ranging from selective C5a inhibitors to dual C5a/IL-8 inhibitors.

Furthermore, quaternary ammonium salts of omega-aminoalkylamides of R-2-aryl-propionic acids have been reported as selective inhibitors of C5a induced neutrophils and monocytes chemotaxis (WO 03/029187).

We have recently described novel classes of "2-arylpropionylsulfonamides" (WO 00/24710) and "2R-arylpropionylamides" (WO 02/58858), "2-arylpropionic acids" (WO 03/043625) and "2-arylacetic acids" (WO 04/069782) as potent and selective inhibitors of CXCL8 induced human PMN chemotaxis. The compounds described in the above patent applications have been found to inhibit CXCL8 induced PMN chemotaxis in a range of concentration between $10^{-7}$ M and $10^{-9}$ M; by contrast the compounds of the invention do not inhibit C5a and f-MLP induced PMN chemotaxis in the same range of concentration.

Next, we have described a novel class of "omega-aminoalkylamides of R-2-aryl-propionic acids as inhibitors of the chemotaxis of polymorphonucleate and mononucleate cells induced by the anaphylatoxin C5a" (WO 02/068377). In this patent application, we have reported that the omega amino group on the N-linked substituent is a crucial requisite (pharmacophoric point) for C5a inhibitory activity. A selected number of compounds of the invention has been found able to inhibit both C5a and CXCL8 induced PMN chemotaxis by virtue of a flexible (2 to 4 atoms) spacer between the amido group and the basic residue. The crucial role of the basic, positively charged moiety for C5a inhibition is confirmed by the activity of corresponding quaternary ammonium salts as described in (WO 03/029187).

DETAILED DESCRIPTION OF THE INVENTION

We have now surprisingly found a selected class of 2-R-arylpropionamides and 2-R-arylpropionylsulfonamides which, even if lacking of the omega-aminoalkyl group, exhibit a potent and selective inhibitory effect on C5a induced human PMN chemotaxis.

We have now found that selected 2-R-arylpropionamides and 2-R-arylpropionylsulfonamides with a HYDROGEN BOND ACCEPTOR atom/group in a well defined position in the chemical space, show a surprising potent inhibitory effect on C5a induced human PMN chemotaxis. Interestingly, these compounds absolutely lack of CXCL8 inhibitory activity.

A pharmacophore is defined as the ensemble of steric and electronic requirements, in a class of biologically active compounds, necessary to ensure the biological activity. In general, the pharmacophore can be considered the ensemble of steric and electronic requirements (features) necessary to ensure positive interactions between a biologically active compound and its biological target.

The pharmacophore model accounting for the inhibition of C5a is depicted in FIG. 1. The novel pharmacophore model shares four out of five features with the previously described pharmacophore of CXCL8 inhibitors (WO 04/069782); the four common features (Features 1-4) are completely superimposable in the 3D chemical space. Feature 5, corresponding to the additional Hydrogen Bond Acceptor Point, is characteristic of the pharmacophore of C5a inhibitors. Mapping Feature 5 makes reason of the high potency but also of the observed C5a/CXCL8 selectivity of the compounds. In fact, all the compounds fully mapping the pharmacophore model in FIG. 1 loose inhibitory effect on CXCL8.

In Table 1 a list of selected examples of potent and selective CXCL8 inhibitors is shown. Compounds lacking of the additional hydrogen bond acceptor group do not exhibit any inhibitory activity on C5a (entries 1, 2 and 3).

Ketoprofen amide and sulfonamide derivatives (entries 4 and 5) have been previously reported to be selective CXCL8 inhibitors with negligible activity on the C5a induced PMN chemotaxis.

It is noteworthy that amide derivatives of Ketoprofen (entries 4 and 5), could well match the C5a pharmacophore hypothesis from the geometrical point of view; in agreement with this observation a moderate inhibitory activity has been observed at high (c=$10^{-6}$M) drug concentration (Table 1).

The carbonyl group of benzophenone is well known to be an extremely weak HYDROGEN BOND ACCEPTOR due to the strong electronwithdrawing effect of the two phenyl groups; hence ketoprofen derivatives fail to match the pharmacophore hypothesis due to the electronic properties of the group. Accordingly, enhancing the hydrogen bond acceptor characteristics of the groups in the region of the HYDROGEN BOND ACCEPTOR feature 5 is well paralleled by the increase of the inhibition potency on C5a (as example see Examples 1-4 listed in Table 2) and by the contemporary loss of activity on CXCL8.

A superimposition model for selected compounds from this novel class of C5a inhibitors is depicted in FIG. 2a and FIG. 2b.

Pharmacophore Generation

Pharmacophore generation has been performed using the Catalyst™ software, version 4.7 (Molecular Simulations, Inc., San Diego, Calif.), which is designed to identify common configurations of the active molecules by means of their chemical features. A configuration is a set of relative locations in 3D space, each associated with a feature type. All the compounds in the training set were described in terms of their chemical functions associated within the 3D space. Furthermore, each chemical moiety can be considered by the software as more than one feature on the basis of the found similarity. For example, an aromatic ring can "establish" both hydrophobic interactions and π-π interactions in the target site and this different behaviour is referred to different features (HYDROPHOBIC, HYDROPHOBIC AROMATIC).

A functional group in a molecule can be associated to more than one feature, depending on its chemical and physical properties, and different functional groups can show behaviour similarity in the interaction with the target so mapping the same feature.

Analysis of the feature definitions and selection of the features is a crucial step in the pharmacophore hypothesis generation. It is well known that the most important forces involved in molecular recognition are represented by electrostatic interactions, hydrogen bonding and hydrophobic interactions. We adopted several features definitions relating the chemical nature of the group to the ability of engaging specific interactions responsible for the biological activity.

FEATURES DEFINITIONS

Hydrogen Bond Acceptor (HBA) (Lipid)

A Hydrogen bond acceptor lipid feature matches the following types of atoms or groups of atoms which are surface accessibility: nitrogen, oxygen, or sulphur (except hypervalent) that have a lone pair and charge less than or equal to zero.

Since a lipid environment was considered, all basic amines (primary, secondary and tertiary) are included in this definition. The hydrogen bond is a highly directional interaction; this feature is so indirectly linked to the theoretical position of the corresponding hydrogen donor. Three hydrogen bond positions are for instance considered on carbonyl group (acceptor), the first two along the ideal positions of the lone pairs and a third one along the C=O bond direction.

Hydrogen Bond Donor (HBD)

A Hydrogen bond donor matches the following types of atoms or groups of atoms which are surface accessible: non-acidic hydroxyls, thiols, acetylenic hydrogen and hydrogen attached to nitrogen (except tetrazoles and trifluoromethyl sulphonamide hydrogen).

A Hydrogen bond donor doesn't match nitrogen that would be protonated due to their high basicity.

Hydrophobic (Aliphatic, Aromatic)

Hydrophobic feature is defined as a contiguous set of atoms that are not adjacent to charged or electronegative atoms, in a conformer such that the atoms have surface accessibility. Hydrophobic groups include: phenyl, cycloalkyl, isopropyl, and methyl.

Nevertheless it has been necessary to distinguish the aromatic hydrophobic feature from the aliphatic one in order to grant a good fitting with biological data.

The former includes only the aromatic atoms, the latter includes only the aliphatic atoms.

A molecule is considered matching a configuration only if possesses a set of relative features and specific conformation such that its features can be superimposed with the corresponding "ideal" locations. A set of features can be considered superimposed if each feature lies within a specific distance on tolerance, from the ideal point.

DESCRIPTION OF THE FIGURES

FIGS. 2a and 2b illustrate superimposition of selected arylpropionic derivatives of Formula I in the pharmacophore model of FIG. 1.

2a) Represented compounds of Formula I are: (R)-2-[(2-oxaxol-2-yl) phenyl]propionamide (example 14), (R)-2-(3-benzenesulfonylphenyl)propionamide (example 19) and N—{(R)-2-[3-furan-2-carbonyl)] propionyl}methanesulfonamide (example 23)

2b) Represented compounds of Formula I are: (R)-2-[3-(2-methoxyphenoxy)phenyl]propionamide (example 10); (R)-

2-[3-(2-methoxyphenylamino)phenyl]propionamide (example 12); (R)-2-[3-(pyridin-2-ylamino)phenyl]propionamide (example 13).

COORDINATES

Figure 1:
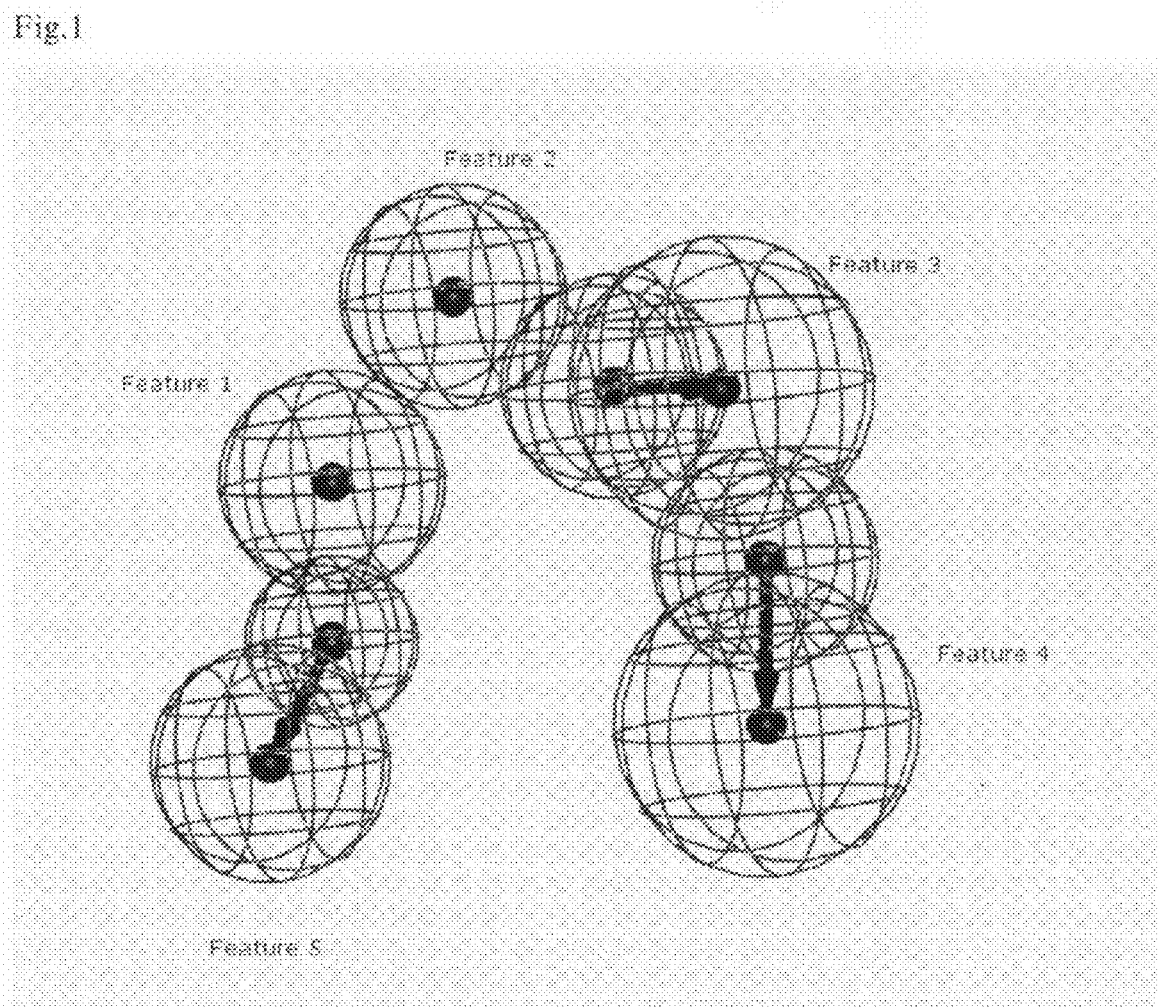
FIG. 1 graphically shows the five pharmacophoric features of C5a inhibitors. The following features types take part in the pharmacophore portion: three Hydrogen Bond Acceptors, one Hydrophobic Aromatic and one Hydrophobic Aliphatic. The (aromatic and aliphatic) hydrophobic features are represented by spheres of 1.7 Angstroms radius. The hydrogen bond acceptor is represented by a vector function consisting two spheres whose centroids are 3.0 Angstroms apart. The smaller (1.7 Angstroms radius) sphere defines the position of the hydrogen bond acceptor atom on the ligand and the larger sphere (2.3 Angstroms) defines the projected point of the hydrogen bond acceptor from the receptor site.
Figure 2B:
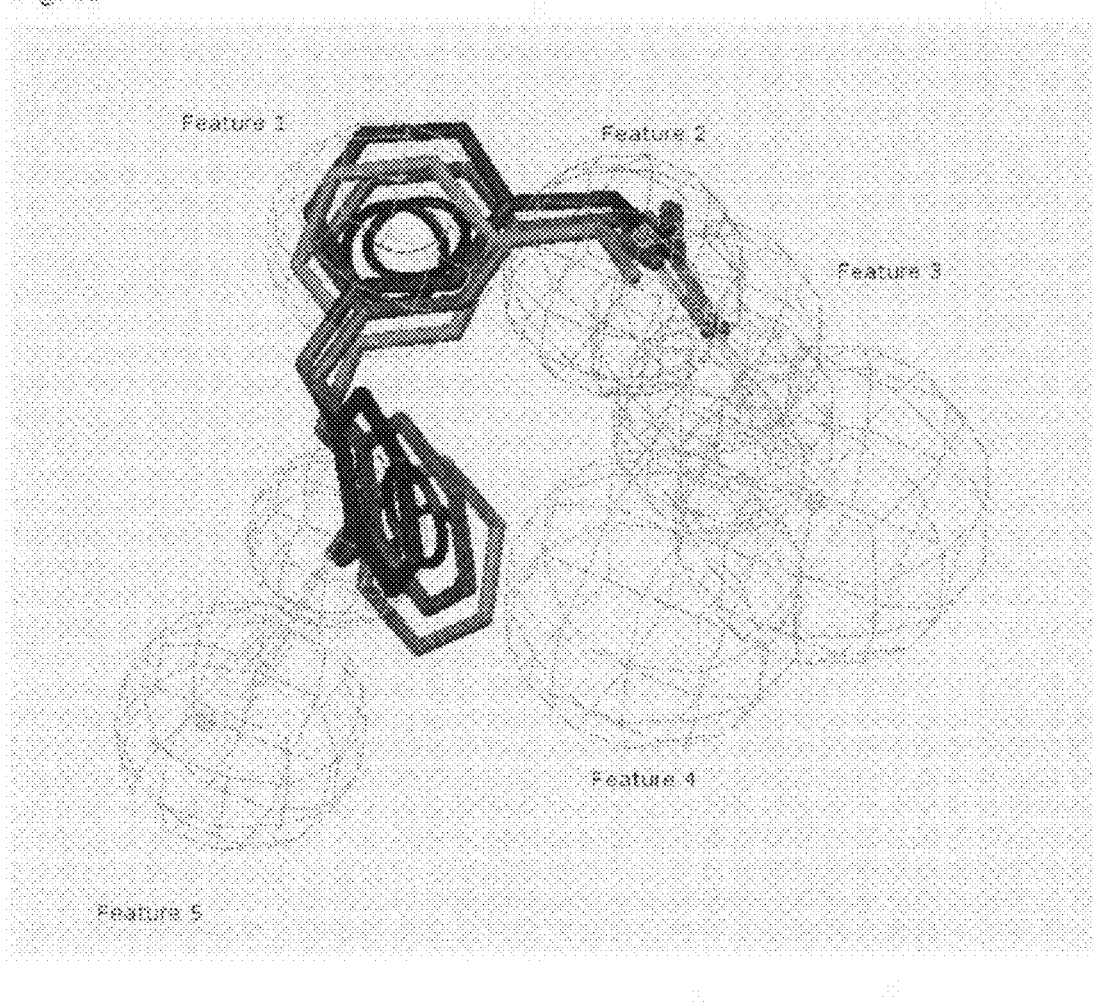

The absolute sphere centroids co-ordinates of each feature in FIG. 1 are listed below:
Common Features
Feature 1
HYDROPHOBIC AROMATIC has Cartesian co-ordinates +2.588, +0.613, −1.940 respectively along XYZ axes.
Feature 2
HYDROPHOBIC ALIFATIC has Cartesian co-ordinates of +1.788, +2.693, +1.260 respectively along XYZ axes.
Feature 3
HYDROGEN BOND ACCEPTOR PROJECTED POINT 1 has Cartesian co-ordinates of −2.713, +2.333, +2.840 respectively along XYZ axes.
HYDROGEN BOND ACCEPTOR ORIGIN 1 has Cartesian co-ordinates of −0.233, +0.936, +1.877 respectively along XYZ axes.
Feature 4
HYDROGEN BOND PROJECTED ACCEPTOR POINT 2 (optional) has Cartesian co-ordinates of −5.013, −1.188, −0.400 respectively along XYZ axes.
HYDROGEN BOND ACCEPTOR ORIGIN 2 (optional) has Cartesian co-ordinates of −2.688, −1.514, +1.472 respectively along XYZ axes.
Feature 5
HYDROGEN BOND ACCEPTOR PROJECTED POINT 3 has Cartesian co-ordinates of −2.093, +3.893, +3.452 respectively along XYZ axes.
HYDROGEN BOND ACCEPTOR ORIGIN 3 has Cartesian co-ordinates of −1.815, +1.640, +1.497 respectively along XYZ axes.

Mapping of the features 1, 2, 3, 5 (HYDROPHOBIC ALIPHATIC, HYDROPHOBIC AROMATIC, HYDROGEN BOND ACCEPTOR 1, HYDROGEN BOND ACCEPTOR 3) is crucial for the biological C5a inhibitory activity of the class.

Feature 4 (HYDROGEN BOND ACCEPTOR 2) can be optionally mapped by the molecules of the class but the presence of the second hydrogen bond acceptor group is not essential.

Tolerances on all the distances between the chemical features have been established in +0.5 Angstroms and tolerances on the geometric angles ±20 degrees.

The present invention relates to (R)-2-aryl-propionamides of formula (I):

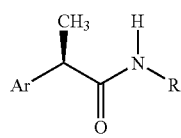

(I)

wherein
Ar is a phenyl group substituited in the 3 (meta) position by a group $R_1$ selected from:
linear or branched $C_1$-$C_8$-alkanoyl, $C_1$-$C_6$-cycloalkanoyl, heteroarylcarbonyl, $C_1$-$C_6$-alkylaminocarbonyl, arylaminocarbonyl, $C_1$-$C_6$-alkylamino, $C_1$-$C_6$-acylamino, arylamino, benzoylamino, aryloxy, heteroaryl, $C_1$-$C_6$-alkoxycarbonyl, $C_1$-$C_6$-aryloxycarbonyl, $C_1$-$C_8$-alkanesulfonyl, arylsulfonyl, or
when $R_1$ is an amino group as defined above, $R_1$ forms a 5-7 membered ring with a further substituent in the 4 position;
R is selected from:
H, OH, $C_1$-$C_5$-alkyl, $C_3$-$C_6$-cycloalkyl, $C_2$-$C_5$-alkenyl, $C_1$-$C_5$-alkoxy;
an heteroaryl group selected from pyridine, pyrimidine, pyrrole, thiofene, furane, indole, thiazole, oxazole;
a α or β carboxyalkyl residue consisting of straight or branched $C_1$-$C_6$-alkyl, $C_3$-$C_6$-cycloalkyl, $C_2$-$C_6$-alkenyl, $C_1$-$C_6$-phenylalkyl, optionally substituted with a further carboxy (COOH) group;
a residue of formula $SO_2Rd$ wherein Rd is $C_1$-$C_6$-alkyl, $C_3$-$C_6$-cycloalkyl, $C_2$-$C_6$-alkenyl, aryl, heteroaryl.
Preferred compounds of the invention are those wherein:
Ar is a phenyl group substituited in the 3 (meta) position by a group $R_1$ selected from:
linear or branched $C_1$-$C_8$-alkanoyl; 2-furyl, 2-oxazolyl, 3-isoxazolyl, 2-benzoxazolyl, 3-benzoisoxazolyl, 2-thiazolyl, 2-pyridyl; furancarbonyl; benzofurancarbonyl; thiophencarbonyl; pyridinecarbonyl; benzoylamino carbonyl; $C_1$-$C_6$-acylamino; benzoylamino; aryloxy; arylamino, or
$R_1$ forms a fused bicyclic system selected from 3-4-dihydro-1H-quinolyl-2-one, 1,3-dihydro-indol-2-one, 1,3,4,5-tetrahydrobenzo[b]azepin-2-one;
R is selected from:
H, OH, $C_1$-$C_5$-alkyl;
2-pyridyl, 2-thiazolyl;
a carboxylalkyl group consisting of straight or branched $C_1$-$C_6$-alkyl, $C_1$-$C_6$-phenylalkyl group;
a residue of formula $SO_2Rd$ wherein Rd is $C_1$-$C_6$-alkyl.
Examples of particularly preferred compounds of formula (I) are:
(R)-2-(3-isobutyrylphenyl)propionamide
(R)-2-(3-cyclopentanecarbonylphenyl)propionamide
(R)-2-[(3-(furan-2-carbonyl)phenyl]propionamide,
(R)-2-[(3-(benzofuran-2-carbonyl)phenyl]propionamide,
(R)-2-[(3-(thiazole-2-carbonyl)phenyl]propionamide,
(R)-2-[(3-(oxazole-2-carbonyl)phenyl]propionamide,
3-((R)-1-carbamoylethyl)-N-(2,6-dichlorophenyl)benzamide,
3-((R)-1-carbamoylethyl)-N-(2,6-dimethylphenyl)benzamide,
3-((R)-1-carbamoylethyl)-N-(3-chloropyridin-2-yl)benzamide,
(R)-2-[3-(2-methoxyphenoxy)phenyl)propionamide,
(R)-2-[3-(2-chlorophenylamino)phenyl]propionamide,
(R)-2-[3-(2-methoxyphenylamino)phenyl]propionamide,
(R)-2-[3-(pyridin-2-ylamino)phenyl]propionamide,
(R)-2-(3-oxazol-2-yl)phenyl]propionamide,
(R)-2-(3-furan-2-yl)phenyl]propionamide,
(R)-2-(oxo-1,2,3,4-tetrahydroquinolin-7-yl)propionamide,
(R)-2-(3-benzenesulfonylphenyl)propionamide.
2-(3-acetylaminophenyl)propionamide,
2-(3-benzoylaminophenyl)propionamide,
N—[(R)-2-(3-cyclopentanecarbonylphenyl)propionyl]methanesulfonamide,
N—{(R)-2-[3-(furan-2-carbonyl)phenyl]propionyl}methanesulfonamide,
N—{(R)-2-[3-(5-methylfuran-2-carbonyl)phenyl]propionyl}methanesulfonamide,
N—{(R)-2-[3-(thiophene-2-carbonyl)phenyl]propionyl}methanesulfonamide, N—{(R)-2-[(3-(benzofuran-2-carbonyl)phenyl]
propionyl}methanesulfonamide,
N—{(R)-2-[(3-(oxazole-2-carbonyl)phenyl]
propionyl}methanesulfonamide,
(R)-2-[3-(furan-2-carbonyl)phenyl]-N-pyrid-2-ylpropionamide,
(R)-2-[3-(furan-2-carbonyl)phenyl]-N-(2H-thiazol-2-yl)propionamide,
(R)-2-[3-(furan-2-carbonyl)phenyl]-N-(4-trifluoromethyl-2H-thiazol-2-yl)propionamide,
(R)-2-[(3-(benzofuran-2-carbonyl)phenyl]-N-(4-trifluoromethyl-2H-thiazol-2-yl)propionamide,
(R)-2-(3-cyclopentanecarbonylphenyl)-N-pyrid-3-ylpropionamide,
(R)-2-[3-(furan-2-carbonyl)phenyl]-N-hydroxypropionamide,
(R)-2-[3-(thiazole-2-carbonyl)phenyl]-N-hydroxypropionamide,
2-{(R)-2-[3-(furan-2-carbonyl)phenyl]-propionylamino}propionic acid,
2-{(R)-2-[3-(furan-2-carbonyl)phenyl]-propionylamino}acetic acid.

The compounds of the invention are potent inhibitors of the human PMNs chemotaxis induced by C5a.

It is therefore a further object of the present invention the use of compounds of formula (I) in the preparation of a medicament for the treatment of diseases that involve C5a induced human PMNs chemotaxis.

Known methods for the preparation of amides and acylsulfonamides (Menschutkin reaction) have been used for the preparation of compounds formula (I); the corresponding carboxylic acids wherein Ar is as above defined, are reacted with amines or sulfonamides of formula $RNH_2$ where R is as above defined in presence of common activating reagents for the carboxylic function according to the methodologies previously described in WO 01/58852; WO 00/24710 and WO 02/068377.

The compounds of the invention of formula (I) were evaluated in vitro for their ability to inhibit chemotaxis of polymorphonucleate leukocytes (hereinafter referred to as PMNs) and monocytes induced by the fractions of the complement C5a and C5a-desArg. For this purpose, to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant fractions C5a and C5a-desArg (Sigma) were used as stimulating agents in the chemotaxis experiments, giving practically identical results.

The lyophilized C5a was dissolved in a volume of HBSS containing 0.2% bovin serum albumin BSA so thus to obtain a stock solution having a concentration of $10^{-5}$ M to be diluted in HBSS to a concentration of $10^{-9}$ M, for the chemotaxis assays.

In the chemotaxis experiments, the PMNs were incubated with the compounds of the invention of formula (I) for 15' at 37° C. in an atmosphere containing 5% $CO_2$. The chemotactic activity of the C5a was evaluated on human circulating polymorphonucleates (PMNs) resuspended in HBSS at a concentration of $1.5 \times 10^6$ PMNs per mL.

During the chemotaxis assay (according to W. Falket et al., J. Immunol. Methods, 33, 239, 1980) PVP-free filters with a porosity of 5 µm and microchambers suitable for replication were used.

The compounds of the invention in formula (I) were evaluated at a concentration ranging between $10^{-7}$ and $10^{-10}$ M; for this purpose they were added, at the same concentration, both to the lower pores and the upper pores of the microchamber. The wells in the lower part contain the solution of C5a or the simple carrier, those in the upper part contain the suspension of PMNs.

Inhibition of C5a-induced chemotactic activity by the individual compounds of the invention of formula (I) was evaluated by incubating the microchamber for the chemotaxis for 60 min at 37° C. in an atmosphere containing 5% $CO_2$.

Evaluation of the ability of the compounds of the invention of formula (I) to inhibit C5a-induced chemotaxis of human monocytes was carried out according to the method disclosed by Van Damme J. et al. (Eur. J. Immunol., 19, 2367, 1989). Inhibition of C5a-induced chemotactic activity by the individual compounds of the invention of formula (I) towards human monocytes was evaluated at a concentration ranging between $10^{-7}$ and $10^{-10}$ M by incubating the microchamber for the chemotaxis for 120 min. at 37° C. in an atmosphere containing 5% $CO_2$.

By way of example, the inhibition data of the chemotaxis of PMN (concentration range between $10^{-7}$ and $10^{-8}$ M) of some representative compounds of the invention are reported in Table 2.

The compounds of formula (I), were evaluated ex vivo in the blood in toto according to the procedure disclosed by Patrignani et al., in J. Pharmacol. Exper. Ther., 271, 1705, 1994. In almost all cases, the compounds of formula (I) do not interfere with the production of $PGE_2$ induced in murine macrophages by lipopolysaccharides stimulation (LPS, 1 µg/mL) at a concentration ranging between $10^{-5}$ and $10^{-7}$ M. Inhibition of the production of $PGE_2$ is mostly at the limit of statistical significance, and generally below 15-20% of the basal value.

It is therefore a further object of the present invention the use of the compounds of the invention as medicaments.

In view of the experimental evidences discussed above and of the role performed by the complement cascade, and namely its fraction C5a, in the processes that involve the activation and the infiltration of neutrophils, the compounds of the invention are particularly useful in the treatment of diseases such as psoriasis (R. J. Nicholoff et al., Am. J. Pathol., 138, 129, 1991), bullous pemphigoid, rheumatoid arthritis (M. Selz et al., J. Clin. Invest., 87, 463, 1981), intestinal chronic inflammatory pathologies such as ulcerative colitis (Y. R. Mahida et al., Clin. Sci., 82, 273, 1992), acute respiratory distress syndrome and idiopathic fibrosis (E. J. Miller, previously cited, and P. C. Carré et al., J. Clin. Invest., 88, 1882, 1991), cystic fibrosis, chronic obstructive pulmonary disease, glomerulonephritis (T. Wada et al., J. Exp. Med., 180, 1135, 1994) and in the prevention and the treatment of injury caused by ischemia and reperfusion.

Furthermore, the compounds of the invention are particularly useful in the treatment of sepsis.

The in vivo activity in the treatment of sepsis has been determined as follows:

Cecal Ligation and Puncture (CLP)

A mouse model of polymicrobial sepsis and tissue injury has been used (according to the procedure disclosed by P. Villa et al., Journal of Endotoxin Research, 1997, 43 (3), 197-204), based on surgically creating a cecal diverticulum, which is then punctured to cause a generalized peritonitis Polymicrobial sepsis caused by cecal ligation and puncture (CLP) in mice produces the inflammatory and pathological sequelae of lung neutrophil infiltration, adult respiratory distress syndrome (ARDS) and death.

Experimental Method

Anesthetized mice were subjected to a 1 cm celiotomy and the cecum isolated. The cecum was ligated below the ileocecal valve (without causing bowel obstruction), punctured on the anti-mesenteric side with an 18 gauge needle, squeezed gently to ascertain that the holes were accessible, and then placed back into the abdomen. The incision was closed and the mice resuscitated with 1 mL saline subcutaneously.

Sham operated controls were similarly treated except that the bowel was not punctured. Antibiotics (gentamicin sulphate 3.2 mg/Kg and clindamycin phosphate 40 mg/kg were injected subcutaneously, once daily, for 3 days starting immediately after surgery. Survival was monitored twice a day for 10 days. Animals were randomised into vehicle or treated groups with 8-15 animals per group.

Representative compounds of the present invention showed activity in treatment of sepsis in a concentration range between 1 and 50 mg/Kg.

To this purpose, the compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

The compounds of the invention can be administered by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day, optionally divided in multiple administrations.

The following examples illustrate the invention.

Materials and Methods

The amines of formula $RNH_2$ used as reagents in the synthesis of compounds of formula (I) are known products, generally commercially available or they can be prepared according to methods described in the literature.

The synthesis of 2-aryl-propionic acids of formula φ-$Ar_3$—C($CH_3$)H—$CO_2$H and of their R-enantiomers is reported in International patent application WO 01/58852. List of abbreviations: THF: tetrahydrofuran; EtOAc: Ethyl acetate; MeOH: methanol; EtOH: ethanol; DCC: 1,3-Dicyclohexylcarbodiimide; DCU: 1,3-Dicyclohexylurea; DBU: 1,8-Diazabicyclo[5.4.0]undec-7-ene.

Preparation of Intermediates of 2-arylpropionic acids

A. 2-[(3-chlorocarbonyl)phenyl]propionitrile

Commercial 2-[(3-carboxy)phenyl]propionitrile (1.0 g, 5.70 mmol) was dissolved in $SOCl_2$ (5 mL) and the resulting solution was left stirring at reflux 3 h. After cooling at room temperature, the mixture was evaporated under reduced pressure to obtain 2-[(3-chlorocarbonyl)phenyl]propionitrile as yellow oil in nearly quantitative yield.

B. 2-(3-aminophenyl)propionitrile

To a solution of 2-[(3-chlorocarbonyl)phenyl]propionitrile (2.5 g, 14.25 mmol) in $CH_2Cl_2$ (15 mL) tetrabutylammonium bromide (0.07 mmol) was added and the mixture cooled to 0° C. Under vigorous stirring a solution of sodium azide (1.275 g, 19.5 mmol) in $H_2O$ (5 mL) was added and the resulting mixture left stirring at 0° C. 2 h. The formed precipitate was filtered off and the organic phase, containing the corresponding acyl azide, washed with $H_2O$ (3×25 mL), dried over $Na_2SO_4$ and used as was for the next step. The organic solution was treated with trifluoroacetic acid (21.38 mmol) and refluxed for 48 h. At the end of the reaction trifluoroacetic acid was evaporated under reduced pressure and the residue diluted with $CH_2Cl_2$ (50 mL) and washed sequentially with a saturated solution of $NaHCO_3$ (2×25 mL) and $H_2O$ (50 mL). After drying over $Na_2SO_4$ and solvent evaporation under reduced pressure 2-[(3-trifluoroacetylamino)phenyl]propionitrile was obtained.

A mixture of 2-[(3-trifluoroacetylamino)phenyl]propionitrile (2.5 g, 9.25 mmol) and $K_2CO_3$ (2.55 g, 17.6 mmol) in $H_2O/CH_3OH$ (3:1) (50 mL) was heated at 60° C. for 16 h. After cooling at room temperature and methanol evaporation, the residual aqueous phase was extracted with $CH_2Cl_2$ (3×25 mL). The collected organic extracts were dried on $Na_2SO_4$ and evaporated under reduced pressure to give 2-(3-aminophenyl)propionitrile as pale yellow oil (1.2 g, 8.32 mmol). Yield 58%.

$^1$H-NMR ($CDCl_3$): δ 7.08 (m, 1H); 6.64 (m, 2H); 6.57 (m, 1H); 3.72 (q, 1H, J=7 Hz); 3.65 (bs, 2H, N$\underline{H}_2$); 1.54 (d, 3H, J=7 Hz).

C. 2-(3-hydroxyphenyl)propionitrile 2-(3-aminophenyl)propionitrile (1.0 g, 6.75 mmol), was suspended in water (12 mL), then under vigorous stirring, $H_2SO_4$ (1.5 ml, 27 mmol) was added dropwise. After stirring 20 min, the mixture was cooled to 4° C., a solution of $NaNO_2$ (0.466 g, 6.75 mmol) in water (5 mL) was added dropwise and the resulting solution was left stirring at reflux 1 h. After cooling at room temperature, ethyl acetate (10 mL) was added to the mixture, the crude was extracted and the organic phase washed with water (3×10 mL) and brine (3×10 mL). After drying over $Na_2SO_4$ and solvent evaporation under reduced pressure 2-(3-hydroxyphenyl)propionitrile was obtained as yellow oil in nearly quantitative yield.

$^1$H-NMR ($CDCl_3$): δ 7.20 (d, 1H); 6.88 (d, 1H, J=7 Hz) 6.80-6.72 (m, 2H); 4.90-4.60 (bs, 1H, OH); 3.75 (q, 1H, J=7 Hz); 1.55 (d, 3H, J=7 Hz).

D. 2-(3-iodophenyl)propionitrile 2-(3-aminophenyl)propionitrile (1.0 g, 6.75 mmol), prepared as previously described, was suspended in water (12 mL) and, under stirring, 37% HCl was added (1.6 mL, 20.2 mmol) drop wise. After 5 min, the mixture was cooled to 4° C., $NaNO_2$ (0.466 g, 6.75 mmol) dissolved in water (5 mL) was added dropwise and the resulting solution was stirred 20 min. To the solution of benzenediazonium chloride derivative, an aqueous solution (5 mL) of KI (1.13 g, 6.76 mmol) was added dropwise at 4° C. and the resulting mixture was allowed stirring 3 h. EtOAc (15 mL) was added to the mixture, the crude was extracted and washed with water (3×10 mL) and brine (3×10 mL). After drying over $Na_2SO_4$ and solvent evaporation under reduced pressure 2-(3-iodophenyl)propionitrile was obtained as yellow oil (1.4 g, 5.4 mmol). Yield 80%.

$^1$H-NMR ($CDCl_3$): δ 7.65 (d, 1H, J=7 Hz); 7.30-7.02 (m, 3H); 3.80 (q, 1H, J=7 Hz); 1.55 (d, 3H, J=7 Hz).

General Procedure for the Optical Resolution to (R) Enantiomers

The optical resolution of all the racemic acids obtained by the below described methods was performed according the procedure described in Akgün, H.; et al., Arzneim.-Forsch./Drug Res. 1996, 46(II), 891-894 and using the most suitable chiral amine.

(R)-2-[3-(isobutyryl)phenyl]propionic acid (I)

The reaction was performed following the procedure described in Grey R— A., J. Org. Chem. 1984, 49, 2288-2289.

To a suspension of $ZnCl_2$ (0.390 g, 2.85 mmol) in 5 mL of dry THF at T=0° C. under nitrogen atmosphere commercial isopropylmagnesium chloride (2M in $Et_2O$, 2.85 mL, 5.70 mmol) was added. After stirring 20 min the catalyst (dppf) $PdCl_2$ (1%, 0.057 mmol) was added and, then, a solution of 2-(chlorocarbonyl)phenylpropionitrile (5.72 mmol), prepared as above described, in dry THF (5 mL) was added dropwise. The mixture was stirred 1 h at 0° C. then 3 h at room temperature. After cooling to 0° C., 3N HCl (10 mL) and $Et_2O$ (30 ml) were added. The aqueous layer was separated and the organic layer washed sequentially with a saturated solution of $NaHCO_3$ (2×30 mL) and brine (30 mL). After drying on $Na_2SO_4$ and solvent evaporation under reduced pressure a residue was obtained that, after flash chromatography (eluent mixture n-hexane/EtOAc 95:5), afforded 2-[3-(isobutyryl)phenyl]propionitrile as pale yellow oil (0.804 g, 4.64 mmol). Yield 81%.

$^1$H-NMR ($CDCl_3$): δ 7.86 (s, 1H); 7.76 (d, 1H, J=7 Hz); 7.45-7.35 (m, 2H); 3.84 (q, 1H, J=7 Hz); 3.45 (m, 1H); 1.68 (d, 3H, J=7 Hz); 1.1 (d, 6H, J=7 Hz).

To a solution of 2-[3-(isobutyryl)phenyl]propionitrile (0.93 g, 4.62 mmol) in 10 mL of dioxane, 37% HCl (10 mL) was added. The mixture was left stirring at 70° C. 4 h. After cooling at room temperature dioxane was evaporated and cold water (10 mL) and EtOAc (15 mL) were added to the residue. The two phases were debated and separated and the organic one was extracted with 1N NaOH (2×5 mL). To the collected basic aqueous extracts, 37% HCl was added to precipitate the acid. At the end of the precipitation 2-[3-(isobutyryl)phenyl]propionic acid was obtained pure by filtration as white solid (0.86 g, 3.95 mmol). Yield 85%.

$[\alpha]_D^{25}$ (c=1, EtOH): −38°; $^1$H-NMR ($CDCl_3$): δ 10.6 (bs, 1H, COOH); 7.86 (s, 1H); 7.76 (d, 1H, J=7 Hz); 7.45-7.35 (m, 2H); 3.79 (q, 1H, J=7 Hz); 3.45 (m, 1H); 1.45 (d, 3H, J=7 Hz); 1.1 (d, 6H, J=7 Hz).

According to the same experimental procedure and using the related commercial Grignard reagents as starting materials, the following compounds were synthesized:

(R)-2-[3-(cyclopentanecarbonyl)phenyl]propionic acid (II)

$[\alpha]_D^{25}$ (c=1, EtOH): −43°; $^1$H-NMR ($CDCl_3$): δ 7.86 (m, 1H); 7.79 (d, 1H, J=7 Hz); 7.52 (d, 1H, J=7 Hz); 7.37 (m, 1H); 3.82 (q, 1H, J=7 Hz); 3.71 (m, 1H); 2.22 (m, 2H); 2.01 (m, 3H); 1.82 (m, 3H); 1.58 (d, 3H, J=7 Hz).

(R)-2-[3-(oxazole-2-carbonyl)phenyl]propionic acid (III)

Starting from the commercial reagent 2-(3-carboxy)phenylpropionitrile and following the procedure described in Harn N. K. et al., Tetrahedron Letters, 1995, 36(52), 9453-9456, 2-[3-(1,3-oxazol-2-ylcarbonyl)phenyl]propionic acid was synthesised.

To a solution of oxazole (0.5 mL, 7.6 mmol) in 50 mL of THF at −78° C. under nitrogen atmosphere n-BuLi (1.6 M in hexanes, 4.7 mL, 7.60 mmol) was added. After stirring 20 min $ZnCl_2$ (2.071 g, 15.2 mmol) was added and the mixture warmed to 0° C. and stirred 45 min. Then CuI (1.45 g, 7.6 mmol) was added and, after 20 min, a solution of 2-(chlorocarbonyl)phenylpropionitrile (15.2 mmol), prepared as previously described, in 10 mL of THF was added by dripping. The mixture was left stirring 2 h. The organic phase was diluted with EtOAc and washed sequentially with a saturated solution of $NaHCO_3$ (2×50 mL) and brine (50 mL). After drying over $Na_2SO_4$ and solvent evaporation under reduced pressure a residue was obtained that, after flash chromatography, afforded 2-[3-(oxazole-2-carbonyl)phenyl]propionitrile as pale yellow oil (1.27 g, 5.63 mmol). Yield 74%.

$^1$H-NMR ($CDCl_3$): δ 8.48 (m, 2H); 7.70 (s, 1H); 7.61 (d, 1H, J=7 Hz); 7.46 (t, 1H, J=7 Hz); 7.28 (s, 1H); 4.03 (q, 1H, J=7 Hz); 1.73 (d, 3H, J=7 Hz).

To a solution of 2-[3-(oxazole-2-carbonyl)phenyl]propionitrile (1 g, 4.43 mmol) in 10 mL of dioxane, 37% HCl (10 mL) was added. The mixture was left under stirring at 70° C. 4 h. After cooling at room temperature dioxane was evaporated and cold water (10 mL) and EtOAc (15 mL) were added to the residue. The two phases were debated and separated and the organic one was extracted with 1N NaOH (2×5 mL). To the collected basic aqueous extracts 37% HCl was added to precipitate the desired acid. At the end of the precipitation pure 2-[3-(oxazole-2-carbonyl)phenyl]propionic acid was obtained by filtration as a white solid (0.87 g, 3.54 mmol). Yield 80%.

$[\alpha]_D^{25}$ (c=1, EtOH): −43° (38%). $^1$H-NMR ($CDCl_3$): δ 8.45 (m, 2H); 7.90 (s, 1H); 7.68 (d, 1H, J=7 Hz); 7.50 (t, 1H, J=7 Hz); 7.38 (s, 1H); 3.90 (q, 1H, J=7 Hz); 1.56 (d, 3H, J=7 Hz).

According to the same experimental procedure and using thiazole as starting reagent, the following compound was synthesised:

(R)-2-[3-(thiazole-2-carbonyl)phenyl]propionic acid (IV)

$[\alpha]_D^{25}$ (c=1, MeOH): −36°. $^1$H-NMR ($CDCl_3$): δ 8.44 (m, 2H); 8.10 (d, 1H, J=3 Hz); 7.73 (d, 1H, J=3 Hz); 7.63 (d, 1H, J=7 Hz); 7.51 (t, 1H, J=7 Hz); 3.90 (q, 1H, J=7 Hz); 1.60 (d, 3H, J=7 Hz).

According to the same experimental procedure and using furan as starting reagent, the following compound was synthesised:

(R)-2-[3-(furan-2-carbonyl)phenyl]propionic acid (V)

$[\alpha]_D^{25}$ (c=1, MeOH): −41°. $^1$H-NMR ($CDCl_3$): δ 7.86 (m, 1H); 7.82 (d, 1H, J=7 Hz); 7.64 (s, 1H); 7.49 (m, 1H); 7.41 (m, 1H); 7.16 (d, 1H, J=7 Hz); 6.53 (m, 1H); 3.79 (q, 1H, J=7 Hz); 1.51 (d, 3H, J=7 Hz).

(R)-2-[3-(benzofuran-2-carbonyl)phenyl]propionic acid (VI)

Starting from the commercial reagent 2-(3-carboxy)phenylpropionitrile and following the procedure described in Galli C., Synthesis, 1979, 303-304, 2-[3-(benzofuran-2-carbonyl)phenyl]propionic acid was synthesised.

To a solution of 2-(3-carboxy)phenylpropionitrile (1.03 g, 5.88 mmol) in 50 mL of dry acetonitrile under nitrogen atmosphere 2,3-benzofuran (1.65 mL, 14.7 mmol) and trifluoroacetic anhydride (3.3 mL, 23.52 mmol) were added. The mixture was left stirring 5 h. The solvent was evaporated under reduced pressure and the residue diluted with CHCl$_3$ and washed sequentially with a saturated solution of NaHCO$_3$ (2×50 mL) and brine (50 mL). After drying over Na$_2$SO$_4$ and solvent evaporation under reduced pressure, a residue was obtained that, after flash chromatography, afforded 2-[3-(benzofuran-2-carbonyl)phenyl]propionitrile as yellow oil (1.05 g, 3.82 mmol). Yield 65%.

$^1$H-NMR (CDCl$_3$): δ 8.04 (m, 2H); 7.76 (d, 1H, J=8 Hz); 7.68-7.54 (m, 5H); 7.36 (m, 1H); 4.03 (q, 1H, J=7 Hz); 1.74 (d, 3H, J=7 Hz).

To a solution of 2-[3-(benzofuran-2-carbonyl)phenyl]propionitrile (1 g, 3.63 mmol) in 10 mL of dioxane, 37% HCl (10 mL) was added. The mixture was left under stirring at 70° C. 4 h. After cooling at room temperature, dioxane was evaporated and cold water (10 mL) and CHCl$_3$ (15 mL) were added to the residue. The two phases were debated and separated and the organic one was extracted with 1N NaOH (2×5 mL). To the collected basic aqueous extracts 37% HCl was added to pH=2 and the acidic phase was extracted back with CHCl$_3$ (3×10 mL). After drying over Na$_2$SO$_4$ and solvent evaporation under reduced pressure pure 2-[3-(benzofuran-2-carbonyl)phenyl]propionic acid was obtained as white powder (1.06 g, 3.60 mmol). Quantitative yield.

$[\alpha]_D^{25}$ (c=1, EtOH): −58° (35%). $^1$H-NMR (CDCl$_3$): δ 7.82 (s, 1H); 7.72 (d, 1H, J=8 Hz); 7.51 (d, 1H, J=8 Hz); 7.42 (d, 2H, J=8 Hz); 7.28 (t, 2H, J=8 Hz); 7.11 (t, 1H, J=8 Hz); 6.38 (m, 1H); 4.23 (bs, 1H, COOH); 3.65 (q, 1H, J=7 Hz); 1.36 (d, 3H, J=7 Hz).

According to the same experimental procedure and using 2-methylfuran as starting reagent, the following compound was synthesised:

(R)-2-[3-(5-methylfuran-2-carbonyl)phenyl]propionic acid (VII)

$[\alpha]_D^{25}$ (c=1, MeOH): −72°. $^1$H-NMR (CDCl$_3$): δ 7.94 (m, 1H); 7.56 (m, 3H); 7.10 (d, 1H, J=4 Hz); 6.25 (d, 1H, J=4 Hz); 3.85 (q, 1H, J=7 Hz); 2.52 (s, 3H); 1.64 (d, 3H, J=7 Hz).

(R)-2-[3-(2,6-dichlorophenylcarbamoyl)phenyl]propionic acid (VIII)

To a solution of commercial 2,6-dichloroaniline (1.4 g, 8.64 mmol) and pyridine (0.69 mL, 8.64 mmol) in 10 ml of dry CH$_2$Cl$_2$ at RT, 2-[(3-chlorocarbonyl)phenyl]propionitrile (1.67 g, 8.64 mmol), prepared as previously described, was added dropwise. The mixture was stirred overnight at RT. The reaction mixture was cooled to 0° C., 1N HCl solution added and the organic phase washed with 1N HCl (2×10 mL). The organic layer was washed sequentially with a saturated solution of NaHCO$_3$ (2×30 mL) and brine (30 mL). After drying over Na$_2$SO$_4$ and solvent evaporation under reduced pressure pure 2-[3-(2,6-dichlorophenylcarbamoyl)phenyl]propionitrile was obtained as yellow oil (1.929 g, 6.05 mmol), yield (70%).

$^1$H-NMR (DMSO-d$_6$): δ 10.4 (bs, 1H, CONH); 8.10-8.25 (m, 2H); 7.80-7.55 (m, 5H); 4.02 (q, 1H, J=7 Hz); 1.55 (d, 3H, J=7 Hz).

To a solution of 2-[3-(2,6-dichlorophenylcarbamoyl)phenyl]propionitrile (1.929 g, 6.05 mmol) in 15 mL of dioxane, 37% HCl (8 mL) was added. The mixture was left under stirring at 40° C. overnight. After cooling at room temperature dioxane was evaporated and cold water (10 mL) and EtOAc (15 mL) were added to the residue. The two phases were debated and separated and the organic one was extracted with 1N NaOH (2×5 mL). To the collected basic aqueous extracts 37% HCl was added to precipitate the desired acid. At the end of the precipitation 2-[3-(2,6-dichlorophenylcarbamoyl)phenyl]propionic acid was obtained pure by filtration as white solid (1.32 g, 3.93 mmol). Yield 40%.

$[\alpha]_D^{25}$ (c=1, EtOH): −320 (30%). $^1$H-NMR (DMSO-d$_6$): δ 10.4 (bs, 1H, CONH); 8.12-8.22 (m, 2H); 7.75-7.60 (m, 5H); 3.95 (q, 1H, J=7 Hz); 1.50 (d, 3H, J=7 Hz).

According to the same experimental procedure and using the related commercial aniline derivatives, the following compounds were synthesised:

(R)-2-[3-(2,6-dimethylphenylcarbamoyl)phenyl]propionic acid (IX)

$[\alpha]_D^{25}$ (c=1, EtOH): −32°. $^1$H-NMR (DMSO-d$_6$): δ 9.75 (bs, 1H, CONH); 8.00-7.90 (m, 2H); 7.60-7.40 (m, 3H); 7.10 (s, 2H); 3.70 (q, 1H, J=7 Hz); 2.15 (s, 6H, J=7 Hz); 1.35 (d, 3H, J=7 Hz).

(R)-2-[3-(3-chloropyridin-2-ylcarbamoyl)phenyl]propionic acid (X)

$[\alpha]_D^{25}$ (c=1, EtOH): −28°. $^1$H-NMR (CDCl$_3$): δ 8.70 (bs, 1H, CONH); 8.20 (d, 1H, J=9 Hz); 7.80-7.68 (m, 3H); 7.40-7.18 (m, 3H); 3.80 (q, 1H, J=7 Hz); 1.58 (d, 3H, J=7 Hz).

(R)-2-{3-[(2-methoxy)phenoxy]phenyl}propionic acid (XI)

The reaction was performed following the procedure described in Evans D. A. et al., Tetrahedron Letters, 1998, 39, 2937-2940.

To a solution of 2-(3-hydroxyphenyl)propionitrile (0.118 g, 0.80 mmol), prepared as above described, in dry CH$_2$Cl$_2$ (6 mL were sequentially added, molecular sieves (4 Å), CuOAc (0.145 mg, 0.80 mmol) and pyridine (0.33 mL, 4.0 mmol). After stirring 20 min commercial 2-methoxyphenylboronic acid (0.243 g 1.60 mmol) was added. The reaction mixture was stirred overnight at room temperature. The reaction mixture was cooled to 0° C., 0.5N HCl added and the organic phase washed (3×10 mL) with 0.5N HCl. After drying over Na$_2$SO$_4$ and solvent evaporation under reduced pressure a residue was obtained that, after flash chromatography (eluent mixture n-hexane/EtOAc 9:1), afforded 2-{3-[(2-methoxy)phenoxy)phenyl]propionitrile as pale yellow oil (0.172 g, 0.68 mmol). Yield 85%.

$^1$H-NMR (CDCl$_3$): δ 7.20-7.10 (m, 2H); 6.98-6.80 (m, 5H); 6.70 (d, 1H, J=7 Hz); 3.75 (s, 3H); 3.48 (q, 1H, J=7 Hz); 1.45 (d, 3H, J=7 Hz).

To a solution of 2-{3-[(2-methoxy)phenoxy)phenyl]propionitrile (0.17 g, 0.68 mmol) in 5 mL of dioxane 37% HCl (5 mL) was added. The mixture was left under stirring at 70° C. 4 h. After cooling at room temperature dioxane was evaporated and cold water (10 mL) and ethyl acetate (10 mL) were added to the residue. The two phases were debated and separated and the organic one was extracted with 1N NaOH (2×5 mL). To the collected basic aqueous extracts 37% HCl was added to precipitate the desired acid. At the end of the precipitation 2-{3-[(2-methoxy)phenoxy)phenyl]propionic acid was obtained pure by filtration as waxy white solid (0.166 g, 0.61 mmol). Yield 90%.

$[\alpha]_D^{25}$ (c=1, EtOH): −41° (38%). $^1$H-NMR (CDCl$_3$): δ 7.22-7.12 (m, 2H); 7.00-6.85 (m, 5H); 6.72 (d, 1H, J=7 Hz); 3.75 (s, 3H); 3.55 (q, 1H, J=7 Hz); 1.50 (d, 3H, J=7 Hz).

(R)-2-[3-(2-chlorophenylamino)phenyl]propionic acid (XII)

Starting from 2-(3-amino)phenylpropionitrile and following the described procedures (Wolfe J. P. et al., J. Am. Chem. Soc., 1996, 118, 7215-7216, Wolfe J. P. et al., Tet. Lett., 1997, 38, 6359-6362, Wolfe J. P. et al., J. Org. Chem., 2000, 65, 1144-1157, Ferreira I. C. F. R. et al., Tetrahedron, 2003, 59, 975-981), 2-[3-(2-chlorophenylamino)phenyl]propionic acid was synthesized.

A mixture of 2-bromochlorobenzene (0.58 mL, 5.5 mmol), 2-(3-amino)phenylpropionitrile (0.72 g, 5 mmol), Pd(OAc)$_2$ (3 mol %), rac BINAP (4 mol %) and Cs$_2$CO$_3$ (2.28 g, 7 mmol) in dry toluene (15 mL) was charged, under Ar atmosphere, in a Schlenk tube and the resulting mixture was heated at 100° C. 20 h. After cooling at room temperature, water (25 mL) and Et$_2$O (25 mL) were added. The phases were separated and the aqueous phase was extracted with Et$_2$O (2×10 mL). After drying over Na$_2$SO$_4$ and solvent evaporation under reduced pressure a residue was obtained that, after flash chromatography, afforded 2-[3-(2-chlorophenylamino)phenyl]propionitrile as colourless oil (0.64 g, 2.5 mmol). Yield 50%.

$^1$H-NMR (CDCl$_3$): δ 7.22 (d, 1H, J=3 Hz); 7.09 (m, 1H); 7.00 (m, 1H); 6.72 (m, 2H); 6.64 (m, 2H); 6.57 (m, 1H); 4.15 (bs, 1H, NH); 3.75 (q, 1H, J=7 Hz); 1.55 (d, 3H, J=7 Hz).

To a solution of 2-[3-(2-chlorophenylamino)phenyl]propionitrile (0.64 g, 2.5 mmol) in dioxane (10 mL) 37% HCl (2 mL) was added. The mixture was left under stirring at 70° C. 4 h. After cooling at room temperature dioxane was evaporated and cold water (10 mL) was added to the residue. The aqueous phase was neutralized with 2N NaOH and extracted (3×10 mL) with CHCl$_3$. After drying over Na$_2$SO$_4$ and solvent evaporation under reduced pressure pure 2-[3-(2-chlorophenylamino)phenyl]propionic acid was obtained as slightly white powder (0.67 g, 2.45 mmol). Yield 98%.

$[\alpha]_D^{25}$ (c=1, MeOH): −42° (30%). $^1$H-NMR (DMSO-d$_6$): δ 7.22 (d, 1H, J=3 Hz); 7.09 (m, 1H); 7.05 (m, 1H); 6.72 (m, 2H); 6.64 (m, 2H); 6.57 (m, 1H); 4.15 (bs, 1H, NH); 3.85 (q, 1H, J=7 Hz); 1.62 (d, 3H, J=7 Hz).

According to the same experimental procedure and using commercial 2-bromoanisole as starting reagent, the following compound was synthesised:

(R)-2-[3-(2-methoxyphenylamino)phenyl]propionic acid (XIII)

$[\alpha]_D^{25}$ (c=1, MeOH): −27°. $^1$H-NMR (DMSO-d$_6$): δ 7.52 (d, 1H, J=7 Hz); 7.25 (m, 1H); 7.08 (m, 1H); 6.80 (m, 2H); 6.62 (m, 2H); 6.50 (m, 1H); 4.15 (bs, 1H, NH); 3.80 (s, 3H); 3.72 (q, 1H, J=7 Hz); 1.52 (d, 3H, J=7 Hz).

According to the same experimental procedure and using commercial 2-bromopyridine as starting reagent, the following compound was synthesised:

(R)-2-[3-(2-pyridin-2-ylamino)phenyl]propionic acid (XIV)

$[\alpha]_D^{25}$ (c=1, MeOH): −31°. $^1$H-NMR (DMSO-d$_6$): δ 8.15 (bs, 1H, CONH); 7.50 (m, 1H); 7.15-6.98 (m, 3H); 6.90 (m, 1H); 6.82 (m, 2H); 6.75 (m, 1H); 3.55 (q, 1H, J=7 Hz); 1.50 (d, 3H, J=7 Hz).

(R)-2-(3-oxazol-2-ylphenyl)propionic acid (XV)

The reaction was performed following the procedure described in Suzuki A. et al., Syn. Commun. 1981, 11, 513-519.

To a solution of 2-(3-iodophenyl)propionitrile (0.6 g, 2.33 mmol) in dry THF (10 mL) Pd(PPh$_3$)$_4$ (4% mol, 0.108 mg) and Na$_2$CO$_3$ (0.493 g, 4.66 mmol) were added sequentially under nitrogen atmosphere. After stirring 20 min commercial 1,3-oxazole-2-boronic acid (0.289 g 2.56 mmol) was added. The reaction mixture was stirred at reflux 4 h. After cooling at room temperature, THF was evaporated under reduced pressure and EtOAc (10 mL) was added to the crude and the organic phase was washed with water (3×10 mL) and brine (3×10 mL). After drying over Na$_2$SO$_4$ and solvent evaporation a residue was obtained that, after flash chromatography (eluent mixture n-hexane/EtOAc 8:2), afforded 2-(3-oxazol-2-ylphenyl) propionitrile as yellow oil (0.360 g, 1.82 mmol). Yield 78%.

$^1$H-NMR (CDCl$_3$): δ 8.09 (s, 1H); 7.98-7.93 (m, 1H); 7.70 (s, 1H); 7.45 (m, 2H); 7.25 (s, 1H); 3.85 (q, 1H, J=7 Hz); 1.58 (d, 3H, J=7 Hz).

To a solution of 2-(3-oxazol-2-ylphenyl)propionitrile (0.360 g, 1.82 mmol) in 5 mL of dioxane 37% HCl (5 mL) was added. The mixture was left under stirring at 70° C. 4 h. After cooling at room temperature dioxane was evaporated and cold water (10 mL) and EtOAc (10 mL) was added to the residue. The two phases were debated and separated and the organic one was extracted with 1N NaOH (2×5 mL). The mixture was acidified to pH=1 with 2N HCl and the crude was extracted with CH$_2$Cl$_2$ (3×10 mL). The organic collected extracts were dried over Na$_2$SO$_4$ and after solvent evaporation under reduced pressure pure 2-(3-oxazol-2-ylphenyl) propionic acid was obtained as colourless oil (0.360 g, 1.66 mmol). Yield 92%.

$[\alpha]_D^{25}$ (c=1, EtOH): −33° (38%). $^1$H-NMR (CDCl$_3$): δ 8.07 (s, 1H); 7.95-7.90 (m, 1H); 7.70 (s, 1H); 7.44 (m, 2H); 7.23 (s, 1H); 3.82 (q, 1H, J=7 Hz); 1.55 (d, 3H, J=7 Hz).

According to the same experimental procedure and using 2-furanboronic acid as starting reagent, the following compound was synthesised:

(R)-2-(3-furan-2-ylphenyl)propionic acid (XVI)

$[\alpha]_D^{25}$ (c=1, EtOH): −32°. $^1$H-NMR (CDCl$_3$): δ 7.68-7.58 (m, 2H); 7.48 (s, 1H); 7.35-7.25 (m, 2H); 6.68 (d, 1H, J=4 Hz); 6.48 (dd, 1H, J$_1$=4 Hz, J$_2$=2 Hz); 3.80 (q, 1H, J=7 Hz); 1.55 (d, 3H, J=7 Hz).

(R)-2-(2-oxo-1,2,3,4-tetrahydroquinolin-7-yl)propionic acid (XVII)

To a solution of 2-(3-aminophenyl)propionitrile (0.500 g, 3.38 mmol), prepared as previously described, in CH$_2$Cl$_2$ (8 mL) a solution of Et$_3$N (0.515 mL, 3.72 mmol) and 3-chloropropionyl chloride (0.355 mL, 3.72 mmol) in CH$_2$Cl$_2$ (4 mL) was added. The reaction mixture was stirred under reflux 5 h. After cooling at room temperature, the mixture was diluted with CH$_2$Cl$_2$ (10 mL) and the organic phase was washed with KH$_2$PO$_4$ buffer solution (pH=5) (3×10 mL) and brine (2×10 mL). After drying over Na$_2$SO$_4$ and solvent evaporation under reduced pressure pure 2-[3-(3-chloropropionylamino)phenyl]propionitrile was obtained as colourless oil (0.654 g, 2.77 mmol). Yield 82%.

$^1$H-NMR (CDCl$_3$): δ 8.00 (bs, 1H, CONH); 7.50-7.46 (m, 2H); 7.20 (m, 1H); 7.05 (d, 1H, J=7 Hz); 3.95 (q, 1H, J=7 Hz); 3.75 (m, 2H); 2.50 (m, 2H); 1.60 (d, 3H, J=7 Hz).

To a solution of 2-[3-(3-chloropropionylamino)phenyl]propionitrile (0.654 g, 2.77 mmol) in CH$_2$Cl$_2$ (8 mL) at 0° C. AlCl$_3$, (1.10 g, 8.31 mmol) was added portionwise. The reaction mixture was stirred 5 min, then was refluxed 8 h. After cooling at 0° C., the mixture was washed with 6N HCl solution (3×10 mL), water (3×10 mL) and brine (2×10 mL). After drying over Na$_2$SO$_4$ and solvent evaporation a crude residue was obtained that, after flash chromatography (eluent mixture n-hexane/EtOAc 85:15), afforded 2-(2-oxo-1,2,3,4-tetrahydro-quinolin-7-yl]propionitrile as yellow oil (0.345 g, 1.72 mmol). Yield 62%.

$^1$H-NMR (CDCl$_3$): δ 8.00 (bs, 1H, CONH); 7.46 (s, 1H); 7.18 (d, 1H, J=7 Hz); 7.05 (d, 1H, J=7 Hz); 3.90 (q, 1H, J=7 Hz); 2.90 (m, 2H); 2.56 (m, 2H); 1.58 (d, 3H, J=7 Hz).

To a solution of 2-(2-oxo-1,2,3,4-tetrahydro-quinolin-7-yl]propionitrile (0.345 g, 1.72 mmol) in 5 mL of dioxane, 37% HCl (5 mL) was added. The mixture was left under stirring at 40° C. overnight. After cooling at room temperature dioxane was evaporated and cold water (10 mL) and EtOAc (15 mL) were added to the residue. The two phases were debated and separated and the organic one was extracted with 1N NaOH (2×5 mL). To the collected basic aqueous extracts 37% HCl was added to precipitate the desired acid. At the end of the precipitation pure 2-(2-oxo-1,2,3,4-tetrahydro-quinolin-7-yl]propionic acid was obtained by filtration as white solid (0.293 g, 1.34 mmol). Yield 78%.

$[α]_D^{25}$ (c=1, EtOH): −40° (35%). $^1$H-NMR (CDCl$_3$): δ 8.02 (bs, 1H, CONH); 7.46 (s, 1H); 7.18 (d, 1H, J=7 Hz); 7.05 (d, 1H, J=7 Hz); 3.86 (q, 1H, J=7 Hz); 2.90 (m, 2H); 2.56 (m, 2H); 1.55 (d, 3H, J=7 Hz).

(R)-2-[3-(benzensulfonyl))phenyl]propionic acid (XVIII)

The reaction was performed following the procedure described in H. Suzuki et al., Tetrahedron Letters 1995, 36, 6239-6242.

To a solution of 2-(3-iodophenyl)propionitrile (0.6 g, 2.33 mmol) in DMF (8 mL) CuI (0.658 g, 3.45 mmol) and commercial benzensulfinic acid sodium salt (0.612 g, 3.73 mmol) were added under nitrogen atmosphere. The mixture was stirred 6 h at 110° C. The progress of the reaction was monitorated by TLC. After cooling at room temperature, water (15 mL) and Et$_2$O (12 mL) were added to the solution and the organic one was separated, washed with brine (3×10 mL) and dried over Na$_2$SO$_4$. Removal of the solvent under reduced pressure left an oily residue, which was purified by chromatography using n-hexane/EtOAc 9:1 to afford 2-[3-benzenesulfonyl)phenyl]propionitrile as pale yellow oil (0.38 g, 1.40 mmol). Yield 60%.

$^1$H-NMR (CDCl$_3$): δ 7.98-7.75 (m, 4H); 7.60-7.35 (m, 5H); 3.55 (q, 1H, J=7 Hz); 1.55 (d, 3H, J=7 Hz).

To a solution of 2-[3-benzenesulfonyl)phenyl]propionitrile (0.38 g, 1.40 mmol) in 5 mL of dioxane 37% HCl (5 mL) was added. The mixture was left under stirring at 70° C. 4 h. After cooling at room temperature dioxane was evaporated and cold water (10 mL) and ethyl acetate (10 mL) were added to the residue. The two phases were debated and separated and the organic one was extracted with 1N NaOH (2×5 mL). To the collected basic aqueous extracts 37% HCl was added to precipitate the desired acid. At the end of the precipitation 2-[3-benzenesulfonyl)phenyl]propionic acid was obtained pure by filtration as white solid (0.324 g, 1.12 mmol). Yield 80%.

$[α]_D^{25}$ (c=1, EtOH): −29°. $^1$H-NMR (CDCl$_3$): 7.96-7.75 (m, 4H); 7.62-7.38 (m, 5H); 3.50 (q, 1H, J=7 Hz); 1.50 (d, 3H, J=7 Hz).

Synthesis of Amides of Formula (I)

EXAMPLE 1

(R)-2-[3-(isobutyryl)phenyl]propionamide (R)-2-(3-isobutyrylphenyl)propionic acid (I) (0.61 g, 2.78 mmol) was dissolved in SOCl$_2$ (5 mL) and the resulting solution was left stirring at reflux 3 h. After cooling at room temperature, the mixture was evaporated under reduced pressure; the crude acyl chloride was diluted with dry THF (5 mL) and cooled at 0-5° C. Gaseous dry ammonia in excess was bubbled into the mixture, under vigorous stirring. The reaction was monitored by TLC; after the complete disappearance of the starting reagent the solvent was evaporated under reduced pressure and the residue was diluted with CHCl$_3$ (10 mL) and water (10 mL); the two phases were debated and separated and the organic one was washed with a saturated solution of NaHCO$_3$ (3×10 mL) and water (2×10 mL), dried over Na$_2$SO$_4$ and evaporated under vacuum to give pure (R)-2-(3-isobutyrylphenyl)propionamide (0.56 g, 2.58 mmol) as colourless oil. Yield 93%.

$[α]_D^{25}$ (c=1, EtOH): −35°. $^1$H-NMR (CDCl$_3$): δ 7.90 (s, 1H); 7.86 (d, 1H, J=7 Hz); 7.52-7.45 (m, 2H); 5.50 (bs, 2H, CONH$_2$); 3.80 (q, 1H, J=7 Hz); 3.45 (m, 1H); 1.50 (d, 3H, J=7 Hz); 1.1 (d, 6H, J=7 Hz).

According to the same experimental procedure and using the corresponding 2-arylpropionic acids above described as starting reagents, the following compounds were synthesized:

EXAMPLE 2

(R)-2-[3-(cyclopentanecarbonyl)phenyl]propionamide $[α]_D^{25}$ (c=1, EtOH): −28°. $^1$H-NMR (CDCl$_3$): δ 7.86 (s, 1H); 7.76 (d, 1H, J=7 Hz); 7.45-7.35 (m, 2H); 5.60-5.50 (bs, 2H, CONH$_2$); 3.75 (q, 1H, J=7 Hz); 3.70 (m, 1H); 2.23 (m, 2H); 2.05 (m, 3H); 1.85 (m, 3H); 1.45 (d, 3H, J=7 Hz).

EXAMPLE 3

(R)-2-[(3-(furan-2-carbonyl)phenyl]propionamide $[α]_D^{25}$ (c=1, MeOH): −41°. $^1$H-NMR (CDCl$_3$): δ 8.10 (d, 1H, J=3 Hz); 7.86 (m, 1H); 7.82 (d, 1H, J=7 Hz); 7.64 (s, 1H); 7.49 (m, 2H); 7.41 (m, 1H); 5.80 (bs, 2H, CONH$_2$); 3.79 (q, 1H, J=7 Hz); 1.41 (d, 3H, J=7 Hz).

EXAMPLE 4

(R)-2-[3-(2-benzofuran-2-carbonyl)phenyl]propionamide $[α]_D^{25}$ (c=1, EtOH): −48°. $^1$H-NMR (CDCl$_3$): δ 8.30 (s, 1H); 8.15 (d, 1H, J=8 Hz); 7.51 (d, 1H, J=8 Hz); 7.42 (d, 2H, J=8 Hz); 7.28 (t, 2H, J=8 Hz); 7.11 (t, 2H, J=8 Hz); 5.25 (bs, 2H, CONH$_2$); 3.65 (q, 1H, J=7 Hz); 1.36 (d, 3H, J=7 Hz).

EXAMPLE 5

(R)-2-[3-(thiazole-2-ylcarbonyl)phenyl]propionamide $[α]_D^{25}$ (c=1, MeOH): −30°. $^1$H-NMR (CDCl$_3$): δ 8.40 (m, 2H); 8.08 (d, 1H, J=3 Hz); 7.75 (d, 1H, J=3 Hz); 7.63 (d, 1H, J=7 Hz); 7.51 (t, 1H, J=7 Hz); 5.55 (bs, 2H, CONH$_2$); 3.88 (q, 1H, J=7 Hz); 1.63 (d, 3H, J=7 Hz).

EXAMPLE 6

(R)-2-[3-(1,3-oxazol-2-ylcarbonyl)phenyl]propionamide $[\alpha]_D^{25}$ (c=1, EtOH): −39°. $^1$H-NMR (CDCl$_3$): δ 8.45 (m, 2H); 7.90 (s, 1H); 7.68 (d, 1H, J=7 Hz); 7.50 (t, 1H, J=7 Hz); 7.38 (s, 1H); 5.66 (bs, 2H, CONH$_2$); 3.90 (q, 1H, J=7 Hz); 1.56 (d, 3H, J=7 Hz).

EXAMPLE 7

3-((R)-1-carbamoylethyl)-N-(2,6-dichlorophenyl)benzamide $[\alpha]_D^{25}$ (c=1, EtOH): −27°. $^1$H-NMR (DMSO-d$_6$): δ 10.4 (bs, 1H, CONH); 8.22-8.12 (m, 2H); 7.75-7.60 (m, 5H); 6.60 (bs, 2H, CONH2); 3.95 (q, 1H, J=7 Hz); 1.50 (d, 3H, J=7 Hz).

EXAMPLE 8

3-((R)-1-carbamoylethyl)-N-(2,6-dimethylphenyl)benzamide $[\alpha]_D^{25}$ (c=1, EtOH): −34°. $^1$H-NMR (DMSO-d$_6$): δ 9.75 (bs, 1H, CONH); 8.00-7.90 (m, 2H); 7.60-7.40 (m, 3H); 7.10 (s, 2H); 5.80 (bs, 2H, CONH$_2$); 3.70 (q, 1H, J=7 Hz); 2.15 (s, 6H); 1.35 (d, 3H, J=7 Hz).

EXAMPLE 9

3-((R)-1-carbamoylethyl)-N-(3-chloropyridin-2-yl)benzamide $[\alpha]_D^{25}$ (c=1, EtOH): −30°. $^1$H-NMR (CDCl$_3$): δ 8.70 (bs, 1H, CONH); 8.20 (d, 1H, J=9 Hz); 7.80-7.68 (m, 3H); 7.40-7.18 (m, 3H); 6.12 (bs, 2H, CONH$_2$); 3.80 (q, 1H, J=7 Hz); 1.58 (d, 3H, J=7 Hz).

EXAMPLE 10

(R)-2-[3-(2-methoxyphenoxy)phenyl]propionamide $[\alpha]_D^{25}$ (c=1, EtOH): −38°. $^1$H-NMR (CDCl$_3$): δ 7.22-7.12 (m, 2H); 7.00-6.85 (m, 5H); 6.72 (d, 1H, J=7 Hz); 5.50-5.20 (bs, 2H, CONH$_2$); 3.75 (s, 3H); 3.55 (q, 1H, J=7 Hz); 1.50 (d, 3H, J=7 Hz).

EXAMPLE 11

(R)-2-[3-(2-chlorophenylamino)phenyl]propionamide $[\alpha]_D^{25}$ (c=1, MeOH): −37°. $^1$H-NMR (DMSO-d$_6$): δ 7.22 (d, 1H, J=3 Hz); 7.09 (m, 1H); 7.05 (m, 1H); 6.72 (m, 2H); 6.64 (m, 2H); 6.57 (m, 1H); 5.60-5.35 (bs, 2H, CONH$_2$); 4.15 (bs, 1H, NH); 3.85 (q, 1H, J=7 Hz); 1.62 (d, 3H, J=7 Hz).

EXAMPLE 12

(R)-2-[3-(2-methoxyphenylamino)phenyl]propionamide $[\alpha]_D^{25}$ (c=1, MeOH): −31°. $^1$H-NMR (DMSO-d$_6$): δ 7.50 (d, 1H, J=7 Hz); 7.28 (m, 1H); 7.10 (m, 1H); 6.78 (m, 2H); 6.60 (m, 2H); 6.50 (m, 1H); 5.58 (bs, 2H, CONH$_2$); 4.15 (bs, 1H, NH); 3.80 (s, 3H); 3.70 (q, 1H, J=7 Hz); 1.50 (d, 3H, J=7 Hz).

EXAMPLE 13

(R)-2-[3-(pyridin-2-ylamino)phenyl]propionamide $[\alpha]_D^{25}$ (c=1, MeOH): −36°. $^1$H-NMR (DMSO-d$_6$): δ 8.15 (bs, 1H, CONH); 7.50 (m, 1H); 7.15-6.98 (m, 3H); 6.88 (m, 1H); 6.82 (m, 2H); 6.75 (m, 1H); 5.58-5.38 (bs, 2H, CONH$_2$); 3.58 (q, 1H, J=7 Hz); 1.52 (d, 3H, J=7 Hz).

EXAMPLE 14

(R)-2-(3-oxazol-2-yl)phenyl]propionamide $[\alpha]_D^{25}$ (c=1, EtOH): −29°. $^1$H-NMR (CDCl$_3$): δ 8.00 (s, 1H); 7.95-7.92 (m, 1H); 7.68 (s, 1H); 7.42 (m, 2H); 7.20 (s, 1H); 5.20 (bs, 2H, CONH$_2$); 3.60 (q, 1H, J=7 Hz); 1.55 (d, 3H, J=7 Hz).

EXAMPLE 15

(R)-2-(3-furan-2-yl)phenyl]propionamide $[\alpha]_D^{25}$ (c=1, EtOH): −36°. $^1$H-NMR (CDCl$_3$): δ 7.68-7.58 (m, 2H); 7.48 (s, 1H); 7.35-7.25 (m, 2H); 6.70 (d, 1H, J=4 Hz); 6.50 (dd, 1H, J$_1$=4 Hz, J$_2$=4 Hz); 5.35 (bs, 2H, CONH$_2$); 3.65 (q, 1H, J=7 Hz); 1.58 (d, 3H, J=7 Hz).

EXAMPLE 16

(R)-2-(oxo-1,2,3,4-tetrahydroquinolin-7-yl)propionamide $[\alpha]_D^{25}$ (c=1, EtOH): −43° $^1$H-NMR (CDCl$_3$): δ 8.00 (bs, 1H, CONH); 7.46 (s, 1H); 7.18 (d, 1H, J=7 Hz); 7.05 (d, 1H, J=7 Hz); 5.70-5.58 (bs, 2H, CONH); 3.90 (q, 1H, J=7 Hz); 2.90 (m, 2H); 2.56 (m, 2H); 1.58 (d, 3H, J=7 Hz).

EXAMPLE 17

(R)-2-(3-benzenesulfonylphenyl)propionamide $[\alpha]_D^{25}$ (c=1, EtOH): −36°. $^1$H-NMR (CDCl$_3$): δ 7.96-7.75 (m, 4H); 7.62-7.38 (m, 5H); 5.65 (bs, 2H, CONH$_2$); 3.50 (q, 1H, J=7 Hz); 1.50 (d, 3H, J=7 Hz).

EXAMPLE 18

2-(3-acetylamino)phenyl propionamide

To a solution of 2-(3-amino)phenylpropionamide (0.2 g, 1.26 mmol) (prepared from 2-(3-amino)phenylpropionitrile as described in Erdelmeier I. et al., J. Org. Chem., 2000, 65, 8152-8157) in 10 mL of dry CH$_2$Cl$_2$ triethylamine (0.19 mL, 1.39 mmol) and acetyl chloride (90 μL; 1.26 mmol) were added. The mixture was left stirring at room temperature for 4 h, washed with H$_2$O (3×15 mL) and dried over Na$_2$SO$_4$. After solvent evaporation under reduced pressure a residue was obtained that, by purification by flash chromatography, afforded 2-(3-acetylamino)phenyl propionamide as transparent oil (0.202 g, 1.01 mmol). Yield 80%.

$^1$H-NMR (CDCl$_3$): δ 8.59 (bs, 1H, CONH); 7.46 (m, 2H); 7.20 (t, 1H, J=8 Hz); 6.97 (d, 1H, J=8 Hz); 5.55 (bs, 2H, CONH$_2$); 3.53 (q, 1H, J=7 Hz); 2.09 (s, 3H); 1.43 (d, 3H, J=7 Hz).

According to the same experimental procedure and using benzoyl chloride as starting reagent, the following compound was synthesised:

EXAMPLE 19

2-(3-benzoylamino)phenyl propionamide $^1$H-NMR (CDCl$_3$): δ 8.59 (bs, 1H, CONH); 8.15 (m, 2H); 7.62 (m, 1H); 7.45 (m, 2H); 7.40 (m, 2H); 7.22 (t, 1H, J=8 Hz); 6.94 (d, 1H, J=8 Hz); 5.55 (bs, 2H, CONH$_2$); 3.53 (q, 1H, J=7 Hz); 1.43 (d, 3H, J=7 Hz).

EXAMPLE 20

N—[(R)-2-(3-cyclopentanecarbonylphenyl)propionyl]methanesulfonamide

The reaction was performed as described in Uehling D. E. et al., J. Med. Chem., 2002, 45(3), 567-583.

1,1'-Carbonyldiimidazole (0.5 g, 3.06 mmol) was added to a solution of (R)-2-[3-(cyclopentanoyl)phenyl]propionic acid (II) (0.68 g, 2.78 mmol) in dry CH$_2$Cl$_2$ (8 mL) and the resulting mixture was left stirring at room temperature for 90 min. Methanesulfonamide (0.26 g, 2.78 mmol) and DBU (0.43 mL, 2.78 mmol) were added and the mixture was left stirring fur further 16 h at room temperature. The organic phase was washed with 0.5N HCl (2×10 mL), with 5% NaH$_2$PO$_4$ (3×10 mL) and with water (2×10 mL). After drying with Na$_2$SO$_4$, solvent was removed under vacuum and the crude was purified by flash chromatography (eluent mixture CH$_2$Cl$_2$/MeOH 95:5). Pure N—[(R)-2-(3-cyclopentanecarbonylphenyl)propionyl]methanesulfonamide 22 was isolated as colourless oil (0.67 g, 2.09 mmol). Yield 790%.

[α]$_D^{25}$ (c=1, EtOH): −48°. $^1$H-NMR (CDCl$_3$): δ 7.80 (m, 2M); 7.42 (m, 2H); 3.68 (m, 2H); 3.15 (s, 3H); 1.88 (m, 4H); 1.62 (m, 4H); 1.43 (d, 3H, J=7 Hz).

According to the same experimental procedure and using the related arylpropionic acids above described, the following compounds were synthesized:

EXAMPLE 21

N—{[(R)-2-[3-(furan-2-carbonyl)phenyl]propionyl}methanesulfonamide

[α]$_D^{25}$ (c=1, EtOH): −23.5°. $^1$H-NMR (CDCl$_3$): δ 7.95 (m, 1H); 7.85 (s, 1H); 7.71 (s, 1H); 7.50 (m, 2H); 7.28 (d, 1H, J=2 Hz); 6.60 (d, 1H, J=2 Hz); 3.82 (q, 1H, J=7 Hz); 3.20 (s, 3H); 1.55 (d, 3H, J=7 Hz).

EXAMPLE 22

N—{[(R)-2-[3-(5-methylfuran-2-carbonyl)phenyl]propionyl}methanesulfonamide

[α]$_D^{25}$ (c=1, EtOH): −15°. $^1$H-NMR (CDCl$_3$): δ 7.95 (m, 1H); 7.84 (m, 2H); 7.48 (bs, 1H+CONH); 7.10 (d, 1H, J=2 Hz); 6.21 (d, 1H, J=2 Hz); 3.80 (q, 1H, J=7 Hz); 3.25 (s, 3H); 2.42 (s, 3H); 1.60 (d, 3H, J=7 Hz).

EXAMPLE 23

N—{[(R)-2-[3-(thiophene-2-carbonyl)phenyl]propionyl}methanesulfonamide

[α]$_D^{25}$ (c=1, EtOH): −37°. $^1$H-NMR (CDCl$_3$): δ 7.80 (m, 1H); 7.71 (m, 2H); 7.58 (m, 1H); 7.40 (m, 2H); 7.10 (m, 1H); 3.75 (q, 1H, J=7 Hz); 3.18 (s, 3H); 1.54 (d, 3H, J=7 Hz).

EXAMPLE 24

N—{[(R)-2-[3-(benzofuran-2-carbonyl)phenyl]propionyl}methanesulfonamide

[α]$_D^{25}$ (c=1, EtOH): −62.5°. $^1$H-NMR (CDCl$_3$): δ 8.05 (m, 1H); 7.95 (s, 1H); 7.75 (m, 1H); 7.69 (m, 1H); 7.55 (m, 4H); 7.30 (m, 1H); 3.85 (q, 1H, J=7 Hz); 3.29 (s, 3H); 1.65 (d, 3H, J=7 Hz).

EXAMPLE 25

N—{[(R)-2-[3-(oxazole-2-carbonyl)phenyl]propionyl}methanesulfonamide

[α]$_D^{25}$ (c=1, EtOH): −83°. $^1$H-NMR (CDCl$_3$): δ 8.48 (m, 1H); 8.35 (s, 1H); 8.05 (bs, 1H, CONH); 7.95 (s, 1H); 7.66 (m, 2H); 7.40 (s, 1H); 3.82 (q, 1H, J=7 Hz); 3.25 (s, 3H); 1.60 (d, 3H, J=7 Hz).

EXAMPLE 26

(R)-2-[3-(furan-2-carbonyl)phenyl]-N-pyrid-2-yl propionamide

Thionyl chloride (0.2 mL, 2.7 mmol) was added to a solution of (R)-2-[3-(2-furan-2-carbonyl)phenyl]propionic acid (V) (0.065 g, 0.27 mmol) in dry CH$_2$Cl$_2$ (5 mL) and the resulting solution was refluxed for 2 h. After cooling at room temperature, toluene and thionyl chloride were removed under vacuum and the residue was dissolved in CH$_2$Cl$_2$ (2 mL); 2-aminopyridine (0.05 g, 0.54 mmol) was added and the solution left stirring overnight at room temperature. The organic solution was washed with water (2×10 mL) and, after drying over Na$_2$SO$_4$, solvent was removed under vacuum and the crude was purified by silica gel chromatography (eluent mixture n-hexane/EtOAc 8:2) to give pure 28 as colourless oil (0.07 g, 0.22 mmol). Yield 80%.

[α]$_D^{25}$ (c=0.6, MeOH): −69°. $^1$H-NMR (CDCl$_3$): δ 8.22 (m, 2H); 8.00 (s, 1H); 7.88 (m, 2H); 7.80 (bs, 1H, CONH); 7.70 (s, 2H); 7.61 (m, 1H); 7.52 (m, 1H); 7.00 (m, 1H); 6.62 (m, 1H); 3.82 (q, 1H, J=7 Hz); 1.65 (d, 3H, J=7 Hz).

According to the same experimental procedure and using the corresponding 2-arylpropionic acids and amine, the following compounds were synthesized:

EXAMPLE 27

(R)-2-[3-(furan-2-carbonyl)phenyl]-N-(2H-thiazol-2-yl)propionamide

[α]$_D^{25}$ (c=0.5, MeOH): −7°. $^1$H-NMR (CDCl$_3$): δ 8.05 (s, 1H); 7.90 (m, 1H); 7.75 (s, 1H); 7.60 (m, 1H); 7.52 (m, 2H); 7.22 (d, 1H, J=2 Hz); 7.02 (d, 1H, J=2 Hz); 6.68 (d, 1H, J=2 Hz); 3.95 (q, 1, J=7 Hz); 1.70 (d, 3H, J=7 Hz).

EXAMPLE 28

(R)-2-[3-(furan-2-carbonyl)phenyl]-N-(4-trifluoromethyl-2H-thiazol-2-yl)propionamide The reagent amine 2-amino-4-trifluoromethyl thiazole was prepared as described in Moazzam M. et al., Indian J. Chem., 1988, 27B(11), 1051-1053.

[α]$_D^{25}$ (c=0.6, MeOH): −11°. $^1$H-NMR (CDCl$_3$): δ 9.35 (bs, 1H, CONH); 7.95 (m, 2H); 7.75 (s, 1H); 7.58-7.39 (m, 2H); 7.30 (s, 1H); 7.25 (s, 1H); 6.55 (s, 1H); 3.96 (q, 1H, J=7 Hz); 1.65 (d, 3H, J=7 Hz).

According to the same experimental procedure and using the arylpropionic acid VI and the amine 2-amino-4-trifluoromethyl thiazole, the following compound was synthesized:

EXAMPLE 29

(R)-2-[3-(benzofuran-2-carbonyl)phenyl]-N-(4-trifluoromethyl-2H-thiazol-2-yl)propionamide $[\alpha]_D^{25}$ (c=1, EtOH): −55°. $^1$H-NMR (CDCl$_3$): 38.85 (bs, 1H, CONH); 8.15 (m, 1H); 8.05 (s, 1H); 7.78 (d, 1H, J=7 Hz); 7.65-7.58 (m, 5H); 7.40 (s, 1H); 7.35 (t, 1H, J=7 Hz); 4.05 (q, 1H, J=7 Hz); 1.80 (d, 3H, J=7 Hz).

According to the same experimental procedure and using the arylpropionic acid II and the amine 2-aminopyridine, the following compound was synthesized:

EXAMPLE 30

(R)-2-(3-cyclopentanecarbonylphenyl)-N-pyrid-2-ylpropionamide $[\alpha]_D^{25}$ (c=1, EtOH): −55°. $^1$H-NMR (CDCl$_3$): δ 8.70 (bs, 1H, CONH); 8.10 (s, 1H); 7.98 (d, 1H, J=3 Hz); 7.84 (m, 1H); 7.80 (d, 1H, J=7 Hz); 7.45 (d, 1H, J=7 Hz); 7.37 (m, 1H); 7.10 (d, 1H, J=3 Hz); 6.95 (m, 1H); 3.75 (q, 1H, J=7 Hz); 3.70 (m, 1H); 2.20 (s, 2H); 2.0 (m, 3H); 1.80 (m, 3H); 1.55 (d, 3H, J=7 Hz).

EXAMPLE 31

(R)-2-[3-(furan-2-carbonyl)phenyl]-N-hydroxypropionamide

Thionyl chloride (1.6 mL, 27 mmol) was added to a solution of (R)-2-[3-(2-furanoyl)phenyl]propionic acid (V) (0.53 g, 2.15 mmol) in dry toluene (10 mL) and the resulting solution was refluxed for 3 h. After cooling at room temperature, toluene and thionyl chloride were removed under vacuum and the residue was dissolved in dry CH$_2$Cl$_2$ (30 mL) and added dropwise to a solution of hydroxylamine hydrochloride (0.179 g, 2.57 mmol) and triethylamine (0.71 mL, 5.14 mmol) in dry CH$_2$Cl$_2$ (10 mL). The resulting solution was left stirring overnight at room temperature. The organic solution was diluted with 1N HCl (20 mL) and, after phase separation, the organic one was washed with water (2×20 mL). After drying over Na$_2$SO$_4$ solvent was removed under vacuum and the crude was purified by chromatography (eluent mixture CHCl$_3$/CH$_3$OH 95:5) to give pure 33 as pale yellow oil (0.65 g, 2.53 mmol). Yield 85%.

$[\alpha]_D^{2}$2 (c=1, MeOH): −44°. $^1$H-NMR (CDCl$_3$): δ 7.92 (m, 2H); 7.75 (s, 1H); 7.57 (m, 1H); 7.50 (t, 1H, J=7 Hz); 7.25 (d, 1H, J=2 Hz); 6.61 (m, 1H); 3.85 (q, 1H, J=7 Hz); 1.95 (bs, 1H, NHOH); 1.62 (d, 3H, J=7 Hz).

According to the same experimental procedure and using the arylpropionic acid IV, the following compound was synthesized:

EXAMPLE 32

(R)-2-[3-(thiazole-2-carbonyl)phenyl]-N-hydroxypropionamide $[\alpha]_D^{25}$ (c=1, MeOH): −28°. $^1$H-NMR (CDCl$_3$): δ 8.44 (m, 2H); 8.12 (d, 1H, J=3 Hz); 7.73 (d, 1H, J=2 Hz); 7.65 (d, 1H, J=7 Hz); 7.50 (t, 1H, J=7 Hz); 3.87 (q, 1H, J=7 Hz); 1.90 (bs, 1H, NHOH); 1.70 (d, 3H, J=7 Hz).

EXAMPLE 33

2-{(R)-2-[3-(furan-2-carbonyl)phenyl]propionylamino}propionic acid

To a solution of (R)-2-[3-(2-furanoyl)phenyl]propionic acid (V) (2 g, 8.2 mmol) in dioxane (5 mL) thionyl chloride (0.92 mL, 12.3 mmol) was added and the resulting solution was heated at reflux for 3 h. After cooling at room temperature the solvent was evaporated and the crude acyl chloride was dissolved in DMF (5 mL) at 0° C. and DCC (1.69 g, 8.2 mmol) and HOBT (1.01 g, 7.5 mmol) were added under stirring. After 30 min. a solution of D,L-alanine methyl ester hydrochloride (1.08 g, 7.5 mmol) and triethylamine (1.01 mL) in DMF (2 mL) was added. The resulting mixture was left stirring for 2 h at 0° C. and overnight at room temperature. The precipitated DCU was filtered off; the filtrate was diluted with EtOAc (15 mL) and the organic phase washed with 10% citric acid buffer (2×10 mL), with a saturated solution of NaHCO$_3$ (2×10 mL) and then with brine (10 mL). After drying over Na$_2$SO$_4$, solvent was evaporated to give a crude that was suspended in n-hexane (20 mL) and left stirring overnight at room temperature. 2-[(R)-2-[3-(furan-2-carbonyl)phenyl]propionylamino]propionic acid methyl ester was isolated by filtration as white powder (1.66 g, 5.7 mmol). Yield 69%. To a solution of the methyl ester in dioxane (3 mL), 1N NaOH (5.7 mL) was added and the mixture left stirring overnight at room temperature. An ice/water mixture (40 mL) was added and the resulting mixture was acidified with conc. H$_2$SO$_4$ to pH=2. The aqueous phase was extracted with CH$_2$Cl$_2$ (4×15 mL) and the collected organic extracts were washed back with brine (15 mL), dried over Na$_2$SO$_4$ and evaporated under vacuum to give an oily residue. 37 was isolated by crystallization from ethyl ether (10 mL) as white solid (0.72 g, 2.28 mmol). Yield 40%.

$[\alpha]_D^{25}$ (c=1, MeOH): −21°. $^1$H-NMR (CDCl$_3$) δ 7.86 (m, 1H), 7.80 (d, 1H, J=7 Hz), 7.64 (s, 1H); 7.47 (m, 1H); 7.35 (m, 1H); 7.16 (d, 1H, J=7 Hz); 6.53 (m, 1H); 5.95 (bs, 1H, CONH); 4.50 (q, 1H, J=7 Hz); 3.65 (q, 1H, J=7 Hz); 1.53 (d, 3H, J=7 Hz), 1.35 (d, 3H, J=7 Hz).

According to the same experimental procedure and using glycine methyl ester hydrochloride, the following compound was synthesized:

EXAMPLE 34

2-{[(R)-2-[3-(furan-2-carbonyl)phenyl]propionylamino}acetic acid $[\alpha]_D^{25}$ (c=1, MeOH): −13.5°. $^1$H-NMR (CDCl$_3$) δ 7.80 (m, 1H), 7.82 (d, 1H, J=7 Hz), 7.64 (s, 1H); 7.47 (m, 1H); 7.33 (m, 1H); 7.15 (d, 1H, J=7 Hz); 6.51 (m, 1H); 5.90 (bs, 1H, CONH); 4.05 (s, 2H); 3.61 (q, 1H, J=7 Hz); 1.53 (d, 3H, J=7 Hz).

TABLE 1

Compounds not active on PMNs C5a induced chemotaxis

| Chemical name | Structure | IL-8 ($10^{-8}$M) | C5a ($10^{-6}$M) |
|---|---|---|---|
| (R)-2-(4-isobutylphenyl)propionamide | [structure: isobutyl-phenyl-CONH₂] | 57 ± 12 | n.a. |
| N-[(R)-2-(4-isobutylphenyl)propionyl]methanesulfonamide | [structure: isobutyl-phenyl-CONHSO₂CH₃] | 65 ± 5 | n.a. |
| (R)-2-(3-isopropylphenyl)propionamide | [structure: 3-isopropyl-phenyl-CONH₂] | 60 ± 5 | n.a. |
| (R)-2-(3-benzoylphenyl)propionamide | [structure: 3-benzoyl-phenyl-CONH₂] | 37 ± 7 | 30 ± 2 |
| N-[(R)-2-(3-benzoylphenyl)propionyl]methanesulfonamide | [structure: 3-benzoyl-phenyl-CONHSO₂CH₃] | 38 ± 5 | 20 ± 5 |

TABLE 2

Compounds active on PMNs C5a induced chemotaxis

| Ex. | Structure | Chemical Name | % inhibition C5a induced PMN migration |
|---|---|---|---|
| 1 | [structure: isobutyryl-phenyl-CONH₂] | (R)-2-(3-isobutyrylphenyl)propionamide | 50 ± 7[a] |
| 2 | [structure: cyclopentanecarbonyl-phenyl-CONH₂] | (R)-2-(3-cyclopentanecarbonylphenyl)propionamide | 59 ± 16[a] |
| 3 | [structure: furan-2-carbonyl-phenyl-CONH₂] | (R)-2-[(3-(furan-2-carbonyl)phenyl]propionamide | 65 ± 6[a] |

TABLE 2-continued

Compounds active on PMNs C5a induced chemotaxis

| Ex. | Structure | Chemical Name | % inhibition C5a induced PMN migration |
|---|---|---|---|
| 4 | 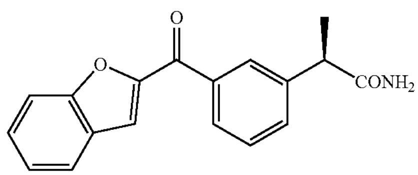 | (R)-2-[(3-(benzofuran-2-carbonyl)phenyl] propionamide | 55 ± 7[b] |
| 5 | 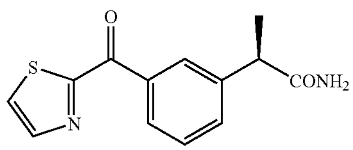 | (R)-2-[(3-(thiazole-2-carbonyl)phenyl] propionamide | 31 ± 7[b] |
| 6 | 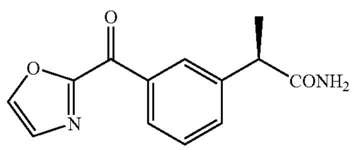 | (R)-2-[(3-(oxazole-2-carbonyl)phenyl] propionamide | 26 ± 6[b] |
| 7 | 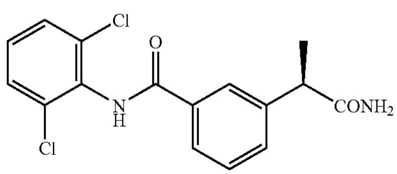 | 3-((R)-1-carbamoylethyl)-N-(2,6-dichlorophenyl)benzamide | 57 ± 8[a] |
| 8 | 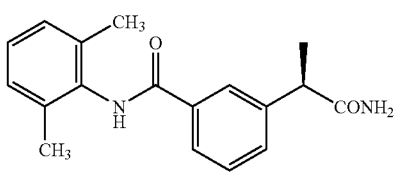 | 3-((R)-1-carbamoylethyl)-N-(2,6-dimethylphenyl)benzamide | 65 ± 10[a] |
| 9 | 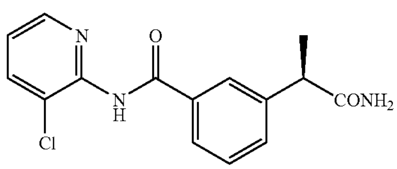 | 3-((R)-1-carbamoylethyl)-N-(3-chloropyridin-2-yl)benzamide | 40 ± 2[a] |
| 10 | 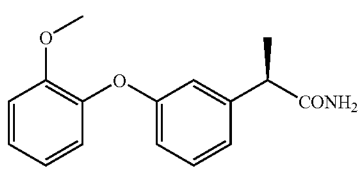 | (R)-2-[3-(2-methoxyphenoxy)phenyl] propionamide | 55 ± 6[b] |
| 11 | 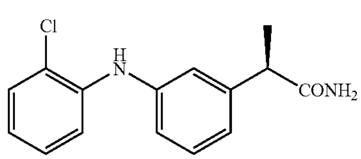 | (R)-2-[3-(2-chlorophenylamino)phenyl] propionamide | 42 ± 5[a] |

TABLE 2-continued

Compounds active on PMNs C5a induced chemotaxis

| Ex. | Structure | Chemical Name | % inhibition C5a induced PMN migration |
|---|---|---|---|
| 12 | 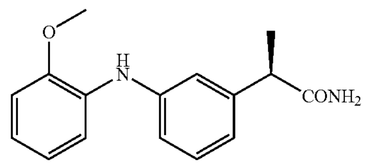 | (R)-2-[3-(2-methoxyphenylamino)phenyl] propionamide | 60 ± 8[a] |
| 13 | 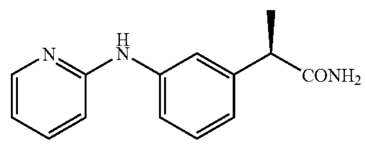 | (R)-2-[3-(pyridin-2-ylamino)phenyl] propionamide | 38 ± 3[a] |
| 14 | 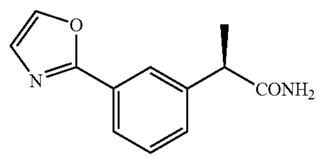 | (R)-2-(3-oxazol-2-yl)phenyl] propionamide | 63 ± 9[a] |
| 15 | 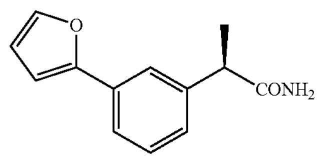 | (R)-2-(3-furan-2-yl)phenyl]] propionamide | 41 ± 7[a] |
| 16 | 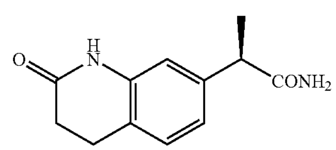 | (R)-2-(oxo-1,2,3,4-tetrahydroquinolin-7-yl) propionamide | 45 ± 10[b] |
| 17 | 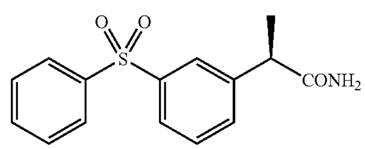 | (R)-2-(3-benzenesulfonylphenyl)propionamide | 54 ± 7[a] |
| 18 | 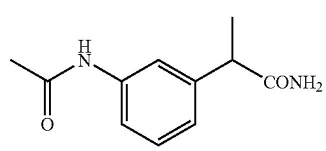 | 2-(3-acetylaminophenyl) propionamide | 83 ± 2[a] |
| 19 | 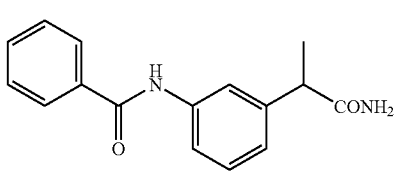 | 2-(3-benzoylaminophenyl) propionamide | 34 ± 11[a] |
| 20 | 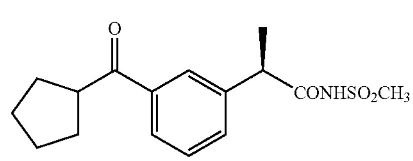 | (R)-2-(3-cyclopentanecarbonylphenyl) propionyl]methanesulfonamide | 22 ± 2[a] |

TABLE 2-continued

Compounds active on PMNs C5a induced chemotaxis

| Ex. | Structure | Chemical Name | % inhibition C5a induced PMN migration |
|---|---|---|---|
| 21 | 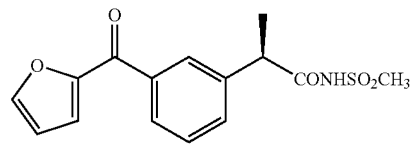 | N-{(R)-2-[3-(furan-2-carbonyl)phenyl]propionyl}methanesulfonamide | 61 ± 15[b] |
| 22 | 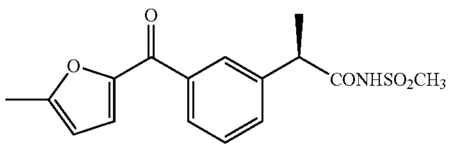 | N-{(R)-2-[3-(5-methylfuran-2-carbonyl)phenyl]propionyl}methanesulfonamide | 53 ± 6[b] |
| 23 | 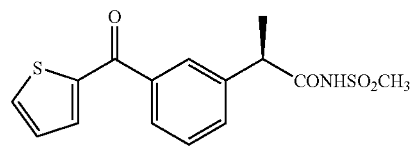 | N-{(R)-2-{(3-(thiophene-2-carbonyl)phenyl]propionyl}methanesulfonamide | 37 ± 11[a] |
| 24 | 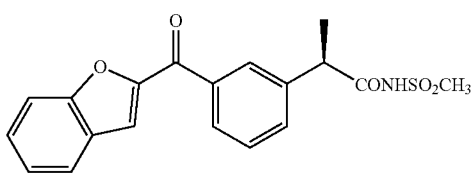 | N-{(R)-2-[(3-(benzofuran-2-carbonyl)phenyl]propionyl}methanesulfonamide | 53 ± 5 |
| 25 | 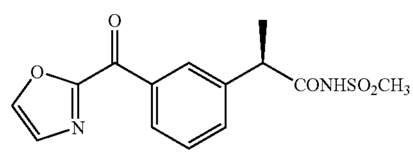 | N-{(R)-2-[(3-(oxazole-2-carbonyl)phenyl]propionyl}methanesulfonamide | 38 ± 8[a] |
| 26 | 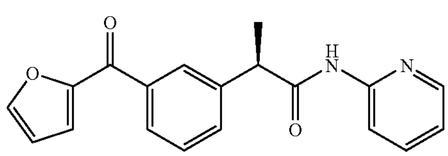 | (R)-2-[3-(furan-2-carbonyl)phenyl]-N-pyrid-2-ylpropionamide | 45 ± 9[b] |
| 27 | 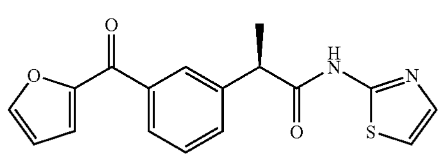 | (R)-2-[3-(furan-2-carbonyl)phenyl]-N-(2H-thiazol-2-yl)propionamide | 60 ± 5[b] |
| 28 | 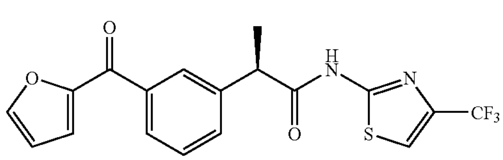 | (R)-2-[3-(furan-2-carbonyl)phenyl]-N-(4-trifluoromethyl-2H-thiazol-2-yl)propionamide | 49 ± 9[b] |
| 29 | 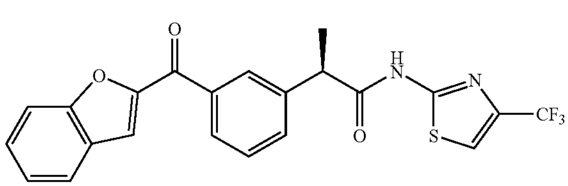 | (R)-2-[(3-(benzofuran-2-carbonyl)phenyl]-N-(4-trifluoromethyl-2H-thiazol-2-yl)propionamide | 40 ± 12[a] |

TABLE 2-continued

Compounds active on PMNs C5a induced chemotaxis

| Ex. | Structure | Chemical Name | % inhibition C5a induced PMN migration |
|---|---|---|---|
| 30 | 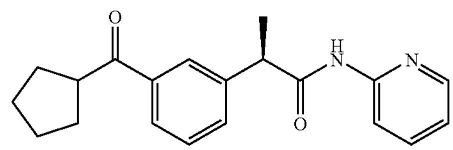 | (R)-2-(3-cyclopentanecarbonylphenyl)-N-pyrid-2-ylpropionamide | 51 ± 5[b] |
| 31 | 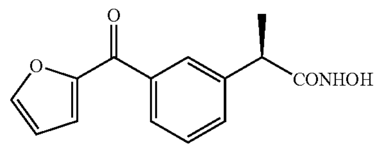 | (R)-2-[3-(furan-2-carbonyl)phenyl]-N-hydroxypropionamide | 70 ± 5[b] |
| 32 | 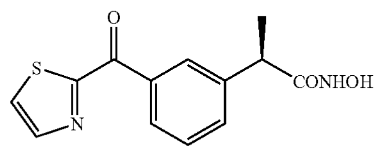 | (R)-2-[3-(thiazole-2-carbonyl)phenyl]-N-hydroxy propionamide | 30 ± 2[b] |
| 33 | 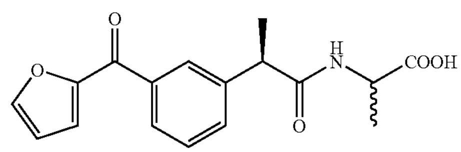 | 2-{(R)-2-[3-(furan-2-carbonyl)phenyl]-propionylamino}propionic acid | 40 ± 5[a] |
| 34 | 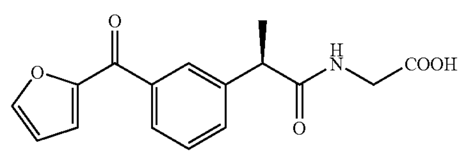 | 2-{(R)-2-[3-(furan-2-carbonyl)phenyl]-propionylamino}acetic acid | 51 ± 7[a] |

[a] drug concentration: $10^{-7}$ M
[b] drug concentration: $10^{-8}$ M

The invention claimed is:

1. An (R)-2 aryl-propionamide compound of formula (I):

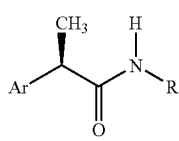

wherein

Ar is a phenyl group substituted at the 3 (meta) position by a group $R_1$ selected from:

a linear or branched $C_1$-$C_8$-alkanoyl, $C_1$-$C_6$-cycloalkanoyl, 2-furyl, 2-oxazolyl, 3-isoxazolyl, 2-benzoxazolyl, 3-benzoisoxazolyl, 2-thiazolyl, 2-pyridyl, furancarbonyl, benzofurancarbonyl, thiophencarbonyl, pyridinecarbonyl, benzolamino carbonyl, $C_1$-$C_6$-aclamino, benzoylamino, aryloxy or arylamino group, or $R_1$ forms a fused bicyclic system selected from 3-4-dihydro-1H-quinolyl-2-one, 1,3-dihydro-indol-2-one and 1,3,4,5-tetrahydrobenzo[b]azepin-2-one;

R is selected from:

H, OH, $C_1$-$C_5$-alkyl, $C_3$-$C_6$-cycloalkyl, $C_2$-$C_5$-alkenyl, $C_1$-$C_5$-alkoxy;

an heteroaryl group selected from pyridine, pyrimidine, pyrrole, thiofene, furane, indole, thiazole, oxazole;

an α or β carboxyalkyl group consisting of straight or branched $C_1$-$C_6$-alkyl, $C_3$-$C_6$-cycloalkyl, $C_2$-$C_6$-alkenyl, $C_1$-$C_6$-phenylalkyl, optionally substituted with a further carboxy (COOH) group; or a group of formula $SO_2Rd$ wherein Rd is $C_1$-$C_6$-alkyl, $C_3$-$C_6$-cycloalkyl, $C_2$-$C_6$-alkenyl, aryl, heteroaryl, with the proviso that compounds of general formula (I) are not:

(R)-2-(3-phenoxyphenyl)-propanoyl-phenylglycine;

(R)-2-(3-phenoxyphenyl)-propanoyl-glycine;

or (R)(-)-2-[(3'-acetyl)phenyl]-N-(4''-pyrimidyl)propionamide.

2. A compound according to claim 1 wherein
R is selected from:
H, OH, $C_1$-$C_5$-alkyl;
2-pyridyl, 2-thiazolyl;
a carboxylalkyl group consisting of straight or branched $C_1$-$C_6$-alkyl, $C_1$-$C_6$-phenylalkyl group; or
a group of formula $SO_2Rd$ wherein Rd is $C_1$-$C_6$-alkyl.

3. The compound according to claim 1 or 2 selected from the group consisting of:
(R)-2-(3-isobutyrylphenyl)pmpionamide,
(R)-2-(3-cyclopentanecarbonylphenyl) propionamide,
(R)-2-[(3-(furan-2-carbonyl)phenyl] propionamide,
(R)-2-[(3-(benzofuran-2-carbonyl)phenyl] propionamide,
(R)-2-[(3-(thiazole-2-carbonyl)phenyl] propionamide,
(R)-2-[(3-(oxazole-2-carbonyl)phenyl] propionamide,
3-((R)-1-carbamoylethyl)-N-(2,6-dichlorophenyl)benzamide,
3-((R)-1-carbamoylethyl)-N-(2,6-dimethylphenyl)benzamide,
3-((R)-1-carbamoylethyl)-N-(3-chloropyridin-2-benzamide,
(R)-2-[3-(2-methoxyphenoxy)phenyl)propionamide,
(R)-2[3-(2-chlorophenylamino)phenyl]propionamide,
(R)-2[3-(2-methoxyphenylamino)phenyl] propionamide,
(R)-2[3-(pyridin-2-ylamino)phenyl] propionamide,
(R)-2-(3-oxazol-2-yl)phenyl] propionamide,
(R)-2-(3-furan-2-yl)phenyl]propionamide,
(R)-2-(oxo-1,2,3,4-tetrahydroquinolin-7-yl) propionamide,
(R)-2-(3-benzenesulfonylphenyl)propionamide,
2-(3-acetylaminophenyl) propionamide,
2-(3-benzoylaminophenyl) propionamide,
N-[(R)-2-(3-cyclopentanecarbonylphenyl) propionyl] methanesulfonamide,
N-{(R)-2-[3-(furan-2-carbonyl)phenyl] propionyl}methanesulfonamide,
N-{(R)-2-[3-(5-methylfuran-2-carbonyl)phenyl] propionyl}methanesulfonamide,
N-{(R)-2-[(3-(thiophene-2-carbonyl)phenyl] propionyl}methanesulfonamide,
N-{(R)-2-[(3-(benzofuran-2-carbonyl)phenyl] propionyl}methanesulfonamide,
N-{(R)-2-[(3-(oxazole-2-carbonyl)phenyl] propionyl}methanesulfonamide,
(R)-2-[3-(furan-2-carbonyl)phenyl]-N-pyrid-2-ylpropionamide,
(R)-2-[3-(furan-2-carbonyl)phenyl]-N-(2H-thiazol-2-yl) propionamide,
(R)-2-[3-(furan-2-carbonyl)phenyl-N-(4-trifluoromethyl-2H-thiazol-2-yl) propionamide,
(R)-2-[(3-(benzofuran-2-carbonyl)phenyl]-N-(4-trifluoromethyl-2H-thiazol-2- Yl)propionamide,
(R)-2-(3-cyclopentanecarbonylphenyl)-N-pyrid-3-ylpropionamide,
(R)-2-[3-(furan-2-carbonyl)phenyl]-N-hydroxypropionamide,
(R)-2-[3-(thiazole-2-carbonyl)phenyl]-N-hydroxypropionamide, 2-{(R)-2-[3-(furan-2-carbonyl)phenyl]-propionylamino}propionic acid, and
2-{(R)-2-[3-(furan-2-carbonyl)phenyl]-propionylamino}acetic acid.

4. A process for the preparation of compounds of formula (I) according to claim 1 comprising reacting a compound of formula (II), $$\text{Ar}-\overset{CH_3}{\underset{}{C}}H-\underset{O}{C}-OH \quad (II)$$

wherein Ar is a phenyl group substituted at the 3 (meta) position by a group $R_1$ wherein $R_1$ has the same meaning as defined in claim 1, with an amine of formula NHR, wherein R has the same meaning as defined in claim 1.

5. A method for treating sepsis comprising administering a compound according to claim 1 to a subject in need thereof.

6. The method of claim 5, wherein the disease is sepsis.

7. A method for treating a disease selected from psoriasis, bullous pemphigoid, rheumatoid arthritis, ulcerative colitis, acute respiratory distress syndrome, idiopathic fibrosis, cystic fibrosis, chronic obstructive pulmonary disease, glomerulonephritis and injury caused by ischemia and reperfusion comprising administering a compound of claim 1.

* * * * *